United States Patent
Badur et al.

(10) Patent No.: US 7,332,649 B2
(45) Date of Patent: Feb. 19, 2008

(54) CHANGING THE FINE CHEMICAL CONTENT IN ORGANISMS BY GENETICALLY MODIFYING THE SHIKIMATE PATHWAY

(75) Inventors: Ralf Badur, Goslar (DE); Michael Geiger, Quedlinburg (DE); Irene Kunze, Gatersleben (DE); Susanne Sommer, Hofheim (DE)

(73) Assignee: SunGene GmbH & Co. KGaA (DE)

( * ) Notice: Subject to any disclaimer, the term of this patent is extended or adjusted under 35 U.S.C. 154(b) by 710 days.

(21) Appl. No.: 10/297,661

(22) PCT Filed: Jun. 28, 2001

(86) PCT No.: PCT/EP01/07391

§ 371 (c)(1),
(2), (4) Date: Dec. 9, 2002

(87) PCT Pub. No.: WO02/00901

PCT Pub. Date: Jan. 3, 2002

(65) Prior Publication Data

US 2006/0057687 A1    Mar. 16, 2006

(30) Foreign Application Priority Data

Jun. 29, 2000  (DE) .................. 100 30 647
Dec. 21, 2000  (DE) .................. 100 64 454

(51) Int. Cl.
C12N 15/84    (2006.01)
C12N 5/14     (2006.01)
A01H 5/10     (2006.01)

(52) U.S. Cl. .................. 800/278; 435/183; 536/23.7; 536/23.2; 800/288

(58) Field of Classification Search ............... 435/69.1, 435/320.1, 468; 530/350, 370; 536/23.2, 536/23; 800/298, 281, 320.3
See application file for complete search history.

(56) References Cited

U.S. PATENT DOCUMENTS 4,956,282 A * 9/1990 Goodman et al. ....... 435/69.51
5,484,716 A * 1/1996 Katsumata et al. ......... 435/108

FOREIGN PATENT DOCUMENTS

| EP | 0 264 914 | 4/1988 |
| WO | WO 91/04263 | 4/1991 |
| WO | WO 97/27285 | 7/1997 |

(Continued)

OTHER PUBLICATIONS

Eberhard et al, "cloning and expression in yeast of a higher plant chorismate mutase" FEBS Lett 334: 233-36.*

(Continued)

*Primary Examiner*—Phuong Bui
*Assistant Examiner*—Brendan O. Baggot
(74) *Attorney, Agent, or Firm*—Connolly Bove Lodge & Hutz LLP

(57) ABSTRACT

The present invention relates to a process for the production of fine chemicals, in particular vitamin E, vitamin K and/or ubiquinone by culturing organisms, in particular plants, whose shikimate pathway is genetically modified over that of the wild type, and to the transgenic organisms themselves.

3 Claims, 6 Drawing Sheets

FOREIGN PATENT DOCUMENTS

Figure 1:
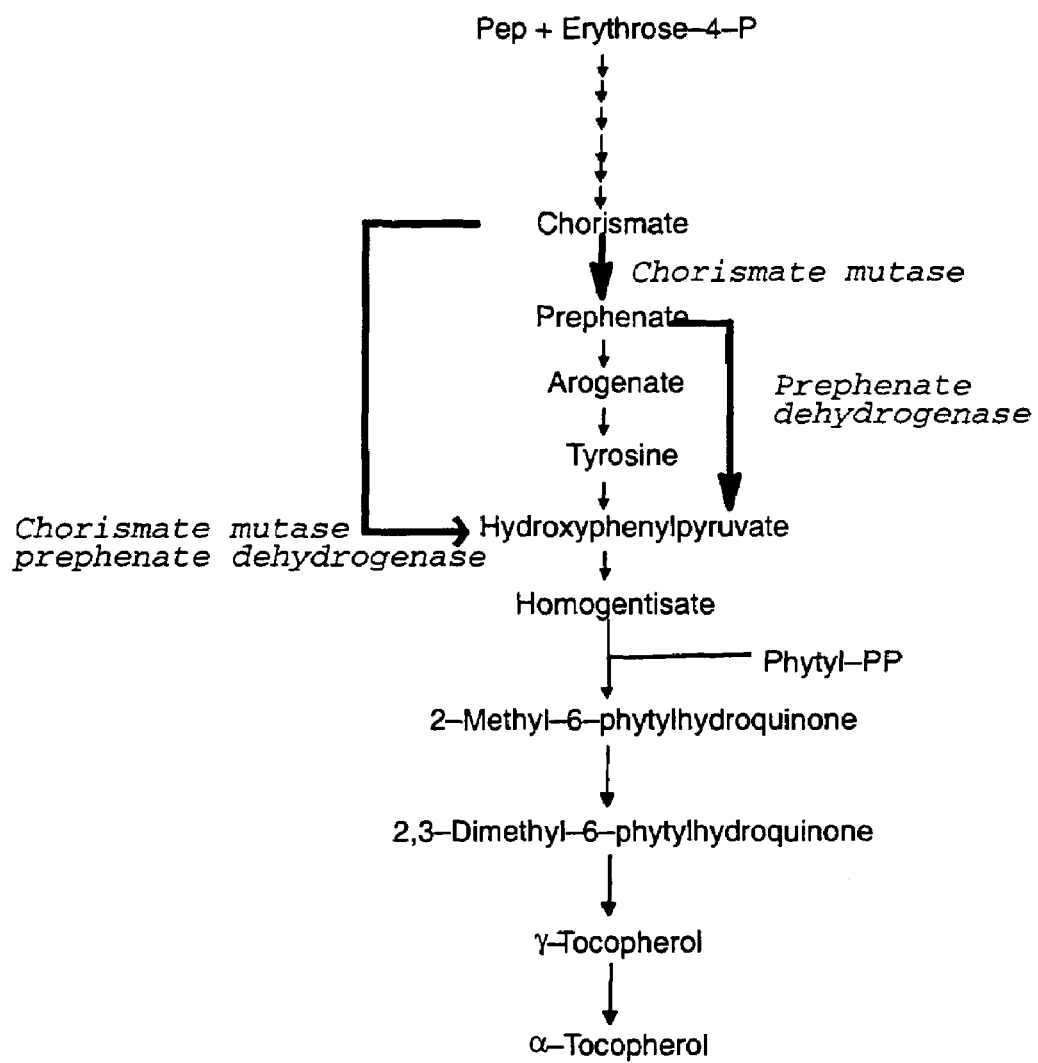

| | | |
|---|---|---|
| WO | WO 99/04622 | 2/1999 |
| WO | WO 99/23231 | 6/1999 |
| WO | WO 00/08169 | 2/2000 |

OTHER PUBLICATIONS

Eberhard, et al, Plant J. (1996) v10 (5) 815-821 "cytosolic and plastidic chorismate mutase . . . ".*

JP Published unexamined patent application Nos. 24192/1985; 260892; /1986; 124375/1986.*

Japanese Published Unexamined Patent Application No. 34197/1985.*

Eberhard et al, "cloning and expression in yeast of a higher plant chorismate mutase" FEBS Lett 334: 233-36.*

Hudson, et al., Nucleotide sequence and transcription of the phenylalanine and tyrosine operons of *Escherichia coli* K12. J. Mol. Biol. 180 (4), 1023-1051 (1984).*

Della Penna, et al., (2006) Vitamin Synthesis in plants: Tocopherol and Carotenoids. Ann. Rev. Plant Biol. 57:711-738.*

Karunanandaa et al., Metabolic Engineering 7:384-400.*

Sutton et al., (1992) Transgenic research, vol. 1, No. 5, pp. 228-236.*

Song et al., (2005) The TyrA family of aromatic-pathway dehydrogenases in phylogenetic context. BMC Biology 3:13, pp. 1-30.*

Bonner, et al., (2004) A core catalytic domain of the TyrA protein family: arogenate dehydrogenase from Synechocystis. Biochem. J. 382:279-291.*

Eberhard et al, "Cytosolic and plastidic chorismate mutase isozymes from *Arabidopsis thaliana*: molecular characterization and enzymatic properties", *The Plant Journal*, vol. 10, No. 5, 1996, pp. 815-821.

Hudson et al, "Nucleotide Sequence and Transcription of the Phenylalanine and Tyrosine Operons of *Escherichia coli* K12", *Journal of Molecular Biology*, vol. 180, No. 4, 1984, pp. 1023-1052.

* cited by examiner

SEQUENCE LISTING

<160> NUMBER OF SEQ ID NOS: 14

<210> SEQ ID NO 1
<211> LENGTH: 1238
<212> TYPE: DNA
<213> ORGANISM: Escherichia coli
<220> FEATURE:
<221> NAME/KEY: CDS
<222> LOCATION: (25)..(1143)

<400> SEQUENCE: 1

```
cccgggtggc ttaagaggtt tatt atg gtt gct gaa ttg acc gca tta cgc        51
                         Met Val Ala Glu Leu Thr Ala Leu Arg
                          1               5 gat caa att gat gaa gtc gat aaa gcg ctg ctg aat tta tta gcg aag        99
Asp Gln Ile Asp Glu Val Asp Lys Ala Leu Leu Asn Leu Leu Ala Lys
 10              15                  20                  25
```

```
cgt ctg gaa ctg gtt gct gaa gtg ggc gag gtg aaa agc cgc ttt gga       147
Arg Leu Glu Leu Val Ala Glu Val Gly Glu Val Lys Ser Arg Phe Gly
             30                  35                  40 ctg cct att tat gtt ccg gag cgc gag gca tct atg ttg gcc tcg cgt       195
Leu Pro Ile Tyr Val Pro Glu Arg Glu Ala Ser Met Leu Ala Ser Arg
             45                  50                  55 cgt gca gag gcg gaa gct ctg ggt gta cca gat ctg att gag gat           243
Arg Ala Glu Ala Glu Ala Leu Gly Val Pro Pro Asp Leu Ile Glu Asp
             60                  65                  70 gtt ttg cgt cgg gtg atg cgt gaa tct tac tcc agt gaa aac gac aaa       291
Val Leu Arg Arg Val Met Arg Glu Ser Tyr Ser Ser Glu Asn Asp Lys
     75                  80                  85 gga ttt aaa aca ctt tgt ccg tca ctg cgt ccg gtg gtt atc gtc ggc       339
Gly Phe Lys Thr Leu Cys Pro Ser Leu Arg Pro Val Val Ile Val Gly
 90                  95                 100                 105 ggt ggc ggt cag atg gga cgc ctg ttc gag aag atg ctg acc ctc tcg       387
Gly Gly Gly Gln Met Gly Arg Leu Phe Glu Lys Met Leu Thr Leu Ser
                110                 115                 120 ggt tat cag gtg cgg att ctg gag caa cat gac tgg gat cga gcg gct       435
Gly Tyr Gln Val Arg Ile Leu Glu Gln His Asp Trp Asp Arg Ala Ala
                125                 130                 135 gat att gtt gcc gat gcc gga atg gtg att gtt agt gtg cca atc cac       483
Asp Ile Val Ala Asp Ala Gly Met Val Ile Val Ser Val Pro Ile His
             140                 145                 150 gtt act gag caa gtt att ggc aaa tta ccg cct tta ccg aaa gat tgt       531
Val Thr Glu Gln Val Ile Gly Lys Leu Pro Pro Leu Pro Lys Asp Cys
     155                 160                 165 att ctg gtc gat ctg gca tca gtg aaa aat ggg cca tta cag gcc atg       579
Ile Leu Val Asp Leu Ala Ser Val Lys Asn Gly Pro Leu Gln Ala Met
170                 175                 180                 185 ctg gtg gcg cat gat ggt ccg gtg ctg ggg cta cac ccg atg ttc ggt       627
Leu Val Ala His Asp Gly Pro Val Leu Gly Leu His Pro Met Phe Gly
                190                 195                 200 ccg gac agc ggt agc ctg gca aag caa gtt gtg gtc tgg tgt gat gga       675
Pro Asp Ser Gly Ser Leu Ala Lys Gln Val Val Val Trp Cys Asp Gly
                205                 210                 215 cgt aaa ccg gaa gca tac caa tgg ttt ctg gag caa att cag gtc tgg       723
Arg Lys Pro Glu Ala Tyr Gln Trp Phe Leu Glu Gln Ile Gln Val Trp
             220                 225                 230 ggc gct cgg ctg cat cgt att agc gcc gtc gag cac gat cag aat atg       771
Gly Ala Arg Leu His Arg Ile Ser Ala Val Glu His Asp Gln Asn Met
             235                 240                 245 gcg ttt att cag gca ctg cgc cac ttt gct act ttt gct tac ggg ctg       819
Ala Phe Ile Gln Ala Leu Arg His Phe Ala Thr Phe Ala Tyr Gly Leu
250                 255                 260                 265 cac ctg gca gaa gaa aat gtt cag ctt gag caa ctt ctg gcg ctc tct       867
His Leu Ala Glu Glu Asn Val Gln Leu Glu Gln Leu Leu Ala Leu Ser
                270                 275                 280 tcg ccg att tac cgc ctt gag ctg gcg atg gtc ggg cga ctg ttt gct       915
Ser Pro Ile Tyr Arg Leu Glu Leu Ala Met Val Gly Arg Leu Phe Ala
             285                 290                 295 cag gat ccg cag ctt tat gcc gac atc att atg tcg tca gag cgt aat       963
Gln Asp Pro Gln Leu Tyr Ala Asp Ile Ile Met Ser Ser Glu Arg Asn
             300                 305                 310 ctg gcg tta atc aaa cgt tac tat aag cgt ttc ggc gag gcg att gag      1011
Leu Ala Leu Ile Lys Arg Tyr Tyr Lys Arg Phe Gly Glu Ala Ile Glu
             315                 320                 325 ttg ctg gag cag ggc gat aag cag gcg ttt att gac agt ttc cgc aag      1059
Leu Leu Glu Gln Gly Asp Lys Gln Ala Phe Ile Asp Ser Phe Arg Lys
```

-continued

```
              330                 335                 340                 345
gtg gag cac tgg ttc ggc gat tac gca cag cgt ttt cag agt gaa agc        1107
Val Glu His Trp Phe Gly Asp Tyr Ala Gln Arg Phe Gln Ser Glu Ser
                      350                 355                 360 cgc gtg tta ttg cgt cag gcg aat gac aat cgc cag taataatcca             1153
Arg Val Leu Leu Arg Gln Ala Asn Asp Asn Arg Gln
                      365                 370 gtgccggatg attcacatca tccggcacct tttcatcagg ttggatcaac aggcactacg      1213
ttctcacttg ggtaacagcg tcgac                                            1238
```

<210> SEQ ID NO 2
<211> LENGTH: 373
<212> TYPE: PRT
<213> ORGANISM: Escherichia coli

<400> SEQUENCE: 2

```
Met Val Ala Glu Leu Thr Ala Leu Arg Asp Gln Ile Asp Glu Val Asp
 1               5                  10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
    290                 295                 300
```

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
            325                 330                 335

Gln Ala Phe Ile Asp Ser Phe Arg Lys Val Glu His Trp Phe Gly Asp
        340                 345                 350

Tyr Ala Gln Arg Phe Gln Ser Glu Ser Arg Val Leu Leu Arg Gln Ala
    355                 360                 365

Asn Asp Asn Arg Gln
    370

<210> SEQ ID NO 3
<211> LENGTH: 1006
<212> TYPE: DNA
<213> ORGANISM: Arabidopsis thaliana
<220> FEATURE:
<221> NAME/KEY: CDS
<222> LOCATION: (64)..(858)

<400> SEQUENCE: 3

```
ctttagcatt gaggaagaag aagaagaaag cttcattttt ccagggggata cagttgaagc      60 ggc atg gca aga gtc ttc gaa tcg gat tcg ggt tct ggt tgt tcc aat       108
    Met Ala Arg Val Phe Glu Ser Asp Ser Gly Ser Gly Cys Ser Asn
    1               5                   10                  15 gta ctg agt ctt gac tta atc aga gaa tcg ttg att agg caa gaa gac       156
Val Leu Ser Leu Asp Leu Ile Arg Glu Ser Leu Ile Arg Gln Glu Asp
                20                  25                  30 acc atc gtc ttc agc ttg atc gag aga gct aag ttt cca ctc aat tct       204
Thr Ile Val Phe Ser Leu Ile Glu Arg Ala Lys Phe Pro Leu Asn Ser
            35                  40                  45 cct gct ttc gag gaa tct cgt tgt cta gat tct gga agt ttc tct tct       252
Pro Ala Phe Glu Glu Ser Arg Cys Leu Asp Ser Gly Ser Phe Ser Ser
        50                  55                  60 ctc act gag ttt ttc gtc aga gag aca gaa atc atc caa gct aag gta       300
Leu Thr Glu Phe Phe Val Arg Glu Thr Glu Ile Ile Gln Ala Lys Val
    65                  70                  75 gga aga tat gaa tac ccg gaa gag aat cct ttc ttc ctt gag aac att       348
Gly Arg Tyr Glu Tyr Pro Glu Glu Asn Pro Phe Phe Leu Glu Asn Ile
80                  85                  90                  95 cct cac tcg gtt ttt cct acg cac aaa tat cca tcg gct ttg cac cct       396
Pro His Ser Val Phe Pro Thr His Lys Tyr Pro Ser Ala Leu His Pro
                100                 105                 110 aag gct cta tct gtt aac att aac aaa caa atc tgg gat att tac ttt       444
Lys Ala Leu Ser Val Asn Ile Asn Lys Gln Ile Trp Asp Ile Tyr Phe
            115                 120                 125 aaa gaa ttg ctt cct ttg ttt gtc aaa cct ggc gat gat ggc aac tat       492
Lys Glu Leu Leu Pro Leu Phe Val Lys Pro Gly Asp Asp Gly Asn Tyr
        130                 135                 140 cca tca act gct gct agt gat ctc gcc tgt tta caa gct ctt tcg aga       540
Pro Ser Thr Ala Ala Ser Asp Leu Ala Cys Leu Gln Ala Leu Ser Arg
    145                 150                 155 agg att cac tac ggt aaa ttt gta gct gag gtc aaa ttc aga gat gct       588
Arg Ile His Tyr Gly Lys Phe Val Ala Glu Val Lys Phe Arg Asp Ala
160                 165                 170                 175 cca caa gat tac gag cct gcg att cgc gct cag gat aga gag gct ttg       636
Pro Gln Asp Tyr Glu Pro Ala Ile Arg Ala Gln Asp Arg Glu Ala Leu
                180                 185                 190 atg aag ctg ttg acg ttt gag aaa gta gaa gaa atg gtt aag aag aga       684
Met Lys Leu Leu Thr Phe Glu Lys Val Glu Glu Met Val Lys Lys Arg
            195                 200                 205
```

```
gtg cag aag aaa gca gaa acg ttt gga caa gaa gta aaa ttc aac tct    732
Val Gln Lys Lys Ala Glu Thr Phe Gly Gln Glu Val Lys Phe Asn Ser
        210                 215                 220 ggc tat ggc gat gag agt aag aag aag tat aaa gtg gat cca ttg ctt    780
Gly Tyr Gly Asp Glu Ser Lys Lys Lys Tyr Lys Val Asp Pro Leu Leu
225                 230                 235 gcc tct cgc atc tac ggg gaa tgg ctt atc cct ctc act aag ctc gtt    828
Ala Ser Arg Ile Tyr Gly Glu Trp Leu Ile Pro Leu Thr Lys Leu Val
240                 245                 250                 255 gag gtt gag tat ctt cta cgt cgt ctc gat tgaatattat ttgtatccaa      878
Glu Val Glu Tyr Leu Leu Arg Arg Leu Asp
                260                 265 atctggccct gttaaagtgg gccttaagtt tttaagtggg cctgttgata tttgtcagga   938
tatgatagaa taattgaatg aagcaacaca gtcatcacta ttttaaattt tgtaagatat   998
tttaagga                                                          1006
```

<210> SEQ ID NO 4
<211> LENGTH: 265
<212> TYPE: PRT
<213> ORGANISM: Arabidopsis thaliana

<400> SEQUENCE: 4

```
Met Ala Arg Val Phe Glu Ser Asp Ser Gly Ser Gly Cys Ser Asn Val
1               5                   10                  15

Leu Ser Leu Asp Leu Ile Arg Glu Ser Leu Ile Arg Gln Glu Asp Thr
            20                  25                  30

Ile Val Phe Ser Leu Ile Glu Arg Ala Lys Phe Pro Leu Asn Ser Pro
        35                  40                  45

Ala Phe Glu Glu Ser Arg Cys Leu Asp Ser Gly Ser Phe Ser Ser Leu
    50                  55                  60

Thr Glu Phe Phe Val Arg Glu Thr Glu Ile Ile Gln Ala Lys Val Gly
65                  70                  75                  80

Arg Tyr Glu Tyr Pro Glu Glu Asn Pro Phe Phe Leu Glu Asn Ile Pro
                85                  90                  95

His Ser Val Phe Pro Thr His Lys Tyr Pro Ser Ala Leu His Pro Lys
            100                 105                 110

Ala Leu Ser Val Asn Ile Asn Lys Gln Ile Trp Asp Ile Tyr Phe Lys
        115                 120                 125

Glu Leu Leu Pro Leu Phe Val Lys Pro Gly Asp Asp Gly Asn Tyr Pro
    130                 135                 140

Ser Thr Ala Ala Ser Asp Leu Ala Cys Leu Gln Ala Leu Ser Arg Arg
145                 150                 155                 160

Ile His Tyr Gly Lys Phe Val Ala Glu Val Lys Phe Arg Asp Ala Pro
                165                 170                 175

Gln Asp Tyr Glu Pro Ala Ile Arg Ala Gln Asp Arg Glu Ala Leu Met
            180                 185                 190

Lys Leu Leu Thr Phe Glu Lys Val Glu Glu Met Val Lys Lys Arg Val
        195                 200                 205

Gln Lys Lys Ala Glu Thr Phe Gly Gln Glu Val Lys Phe Asn Ser Gly
    210                 215                 220

Tyr Gly Asp Glu Ser Lys Lys Lys Tyr Lys Val Asp Pro Leu Leu Ala
225                 230                 235                 240

Ser Arg Ile Tyr Gly Glu Trp Leu Ile Pro Leu Thr Lys Leu Val Glu
                245                 250                 255
```

-continued

Val Glu Tyr Leu Leu Arg Arg Leu Asp
            260                 265

<210> SEQ ID NO 5
<211> LENGTH: 993
<212> TYPE: DNA
<213> ORGANISM: Artificial Sequence
<220> FEATURE:
<223> OTHER INFORMATION: Description of artificial sequence: chimeric
      nucleic acid: transit peptide of plastid
      chorismate mutase + coding sequence of cytosolic
      chorismate mutase
<220> FEATURE:
<221> NAME/KEY: CDS
<222> LOCATION: (1)..(993)

<400> SEQUENCE: 5

```
atg aga tcg tct tgt tgc tcc tct gcg att ggt ggg ttc ttc gac cat        48
Met Arg Ser Ser Cys Cys Ser Ser Ala Ile Gly Gly Phe Phe Asp His
  1               5                  10                  15 cga cgt gaa tta tca acc tca aca ccc att tcc act ctt ctt cct ctt        96
Arg Arg Glu Leu Ser Thr Ser Thr Pro Ile Ser Thr Leu Leu Pro Leu
             20                  25                  30 cca tca acc aaa tct tct ttc tct gtt cgt tgt tct ctt cct cag cca       144
Pro Ser Thr Lys Ser Ser Phe Ser Val Arg Cys Ser Leu Pro Gln Pro
         35                  40                  45 tca aag cca cgc tct gga acc agc tct gtt cac gcc gtt atg aca ctc       192
Ser Lys Pro Arg Ser Gly Thr Ser Ser Val His Ala Val Met Thr Leu
     50                  55                  60 gcc atg gca aga gtc ttc gaa tcg gat tcg ggt tct ggt tgt tcc aat       240
Ala Met Ala Arg Val Phe Glu Ser Asp Ser Gly Ser Gly Cys Ser Asn
 65                  70                  75                  80 gta ctg agt ctt gac tta atc aga gaa tcg ttg att agg caa gaa gac       288
Val Leu Ser Leu Asp Leu Ile Arg Glu Ser Leu Ile Arg Gln Glu Asp
                 85                  90                  95 acc atc gtc ttc agc ttg atc gag aga gct aag ttt cca ctc aat tct       336
Thr Ile Val Phe Ser Leu Ile Glu Arg Ala Lys Phe Pro Leu Asn Ser
            100                 105                 110 cct gct ttc gag gaa tct cgt tgt cta gat tct gga agt ttc tct tct       384
Pro Ala Phe Glu Glu Ser Arg Cys Leu Asp Ser Gly Ser Phe Ser Ser
        115                 120                 125 ctc act gag ttt ttc gtc aga gag aca gaa atc atc caa gct aag gta       432
Leu Thr Glu Phe Phe Val Arg Glu Thr Glu Ile Ile Gln Ala Lys Val
    130                 135                 140 gga aga tat gaa tac ccg gaa gag aat cct ttc ttc ctt gag aac att       480
Gly Arg Tyr Glu Tyr Pro Glu Glu Asn Pro Phe Phe Leu Glu Asn Ile
145                 150                 155                 160 cct cac tcg gtt ttt cct acg cac aaa tat cca tcg gct ttg cac cct       528
Pro His Ser Val Phe Pro Thr His Lys Tyr Pro Ser Ala Leu His Pro
                165                 170                 175 aag gct cta tct gtt aac att aac aaa caa atc tgg gat att tac ttt       576
Lys Ala Leu Ser Val Asn Ile Asn Lys Gln Ile Trp Asp Ile Tyr Phe
            180                 185                 190 aaa gaa ttg ctt cct ttg ttt gtc aaa cct ggc gat gat ggc aac tat       624
Lys Glu Leu Leu Pro Leu Phe Val Lys Pro Gly Asp Asp Gly Asn Tyr
        195                 200                 205 cca tca act gct gct agt gat ctc gcc tgt tta caa gct ctt tcg aga       672
Pro Ser Thr Ala Ala Ser Asp Leu Ala Cys Leu Gln Ala Leu Ser Arg
    210                 215                 220 agg att cac tac ggt aaa ttt gta gct gag gtc aaa ttc aga gat gct       720
Arg Ile His Tyr Gly Lys Phe Val Ala Glu Val Lys Phe Arg Asp Ala
225                 230                 235                 240
```

| | | | | | | | | | | | | | | | |
|---|---|---|---|---|---|---|---|---|---|---|---|---|---|---|---|
| cca | caa | gat | tac | gag | cct | gcg | att | cgc | gct | cag | gat | aga | gag | gct | ttg | 768 |
| Pro | Gln | Asp | Tyr | Glu | Pro | Ala | Ile | Arg | Ala | Gln | Asp | Arg | Glu | Ala | Leu |
| | | | 245 | | | | | 250 | | | | | 255 | | |
| atg | aag | ctg | ttg | acg | ttt | gag | aaa | gta | gaa | gaa | atg | gtt | aag | aag | aga | 816 |
| Met | Lys | Leu | Leu | Thr | Phe | Glu | Lys | Val | Glu | Glu | Met | Val | Lys | Lys | Arg |
| | | 260 | | | | | 265 | | | | | 270 | | | |
| gtg | cag | aag | aaa | gca | gaa | acg | ttt | gga | caa | gaa | gta | aaa | ttc | aac | tct | 864 |
| Val | Gln | Lys | Lys | Ala | Glu | Thr | Phe | Gly | Gln | Glu | Val | Lys | Phe | Asn | Ser |
| | 275 | | | | | 280 | | | | | 285 | | | | |
| ggc | tat | ggc | gat | gag | agt | aag | aag | aag | tat | aaa | gtg | gat | cca | ttg | ctt | 912 |
| Gly | Tyr | Gly | Asp | Glu | Ser | Lys | Lys | Lys | Tyr | Lys | Val | Asp | Pro | Leu | Leu |
| 290 | | | | | 295 | | | | | 300 | | | | | |
| gcc | tct | cgc | atc | tac | ggg | gaa | tgg | ctt | atc | cct | ctc | act | aag | ctc | gtt | 960 |
| Ala | Ser | Arg | Ile | Tyr | Gly | Glu | Trp | Leu | Ile | Pro | Leu | Thr | Lys | Leu | Val |
| 305 | | | | 310 | | | | | 315 | | | | | 320 | |
| gag | gtt | gag | tat | ctt | cta | cgt | cgt | ctc | gat | tga | | | | | | 993 |
| Glu | Val | Glu | Tyr | Leu | Leu | Arg | Arg | Leu | Asp |
| | | | 325 | | | | | 330 | | |

<210> SEQ ID NO 6
<211> LENGTH: 330
<212> TYPE: PRT
<213> ORGANISM: Artificial Sequence
<220> FEATURE:
<223> OTHER INFORMATION: Description of artificial sequence: chimeric;
      transit peptide of plastid
      chorismate mutase + coding sequence of cytosolic
      chorismate mutase

<400> SEQUENCE: 6

Met Arg Ser Ser Cys Cys Ser Ser Ala Ile Gly Gly Phe Phe Asp His
 1               5                  10                  15

Arg Arg Glu Leu Ser Thr Ser Thr Pro Ile Ser Thr Leu Leu Pro Leu
            20                  25                  30

Pro Ser Thr Lys Ser Ser Phe Ser Val Arg Cys Ser Leu Pro Gln Pro
        35                  40                  45

Ser Lys Pro Arg Ser Gly Thr Ser Ser Val His Ala Val Met Thr Leu
    50                  55                  60

Ala Met Ala Arg Val Phe Glu Ser Asp Ser Gly Ser Gly Cys Ser Asn
65                  70                  75                  80

Val Leu Ser Leu Asp Leu Ile Arg Glu Ser Leu Ile Arg Gln Glu Asp
                85                  90                  95

Thr Ile Val Phe Ser Leu Ile Glu Arg Ala Lys Phe Pro Leu Asn Ser
            100                 105                 110

Pro Ala Phe Glu Glu Ser Arg Cys Leu Asp Ser Gly Ser Phe Ser Ser
        115                 120                 125

Leu Thr Glu Phe Phe Val Arg Glu Thr Glu Ile Ile Gln Ala Lys Val
    130                 135                 140

Gly Arg Tyr Glu Tyr Pro Glu Glu Asn Pro Phe Phe Leu Glu Asn Ile
145                 150                 155                 160

Pro His Ser Val Phe Pro Thr His Lys Tyr Pro Ser Ala Leu His Pro
                165                 170                 175

Lys Ala Leu Ser Val Asn Ile Asn Lys Gln Ile Trp Asp Ile Tyr Phe
            180                 185                 190

Lys Glu Leu Leu Pro Leu Phe Val Lys Pro Gly Asp Asp Gly Asn Tyr
        195                 200                 205

Pro Ser Thr Ala Ala Ser Asp Leu Ala Cys Leu Gln Ala Leu Ser Arg
    210                 215                 220

```
Arg Ile His Tyr Gly Lys Phe Val Ala Glu Val Lys Phe Arg Asp Ala
225                 230                 235                 240

Pro Gln Asp Tyr Glu Pro Ala Ile Arg Ala Gln Asp Arg Glu Ala Leu
            245                 250                 255

Met Lys Leu Leu Thr Phe Glu Lys Val Glu Met Val Lys Lys Arg
        260                 265                 270

Val Gln Lys Lys Ala Glu Thr Phe Gly Gln Glu Val Lys Phe Asn Ser
    275                 280                 285

Gly Tyr Gly Asp Glu Ser Lys Lys Tyr Lys Val Asp Pro Leu Leu
        290                 295                 300

Ala Ser Arg Ile Tyr Gly Glu Trp Leu Ile Pro Leu Thr Lys Leu Val
305                 310                 315                 320

Glu Val Glu Tyr Leu Leu Arg Arg Leu Asp
                325                 330

<210> SEQ ID NO 7
<211> LENGTH: 218
<212> TYPE: DNA
<213> ORGANISM: Arabidopsis thaliana
<220> FEATURE:
<221> NAME/KEY: CDS
<222> LOCATION: (20)..(217)

<400> SEQUENCE: 7
ggtaccggcg tcattgttg atg aga tcg tct tgt tgc tcc tct gcg att ggt      52
                    Met Arg Ser Ser Cys Cys Ser Ser Ala Ile Gly
                     1               5                  10 ggg ttc ttc gac cat cga cgt gaa tta tca acc tca aca ccc att tcc     100
Gly Phe Phe Asp His Arg Arg Glu Leu Ser Thr Ser Thr Pro Ile Ser
            15                  20                  25 act ctt ctt cct ctt cca tca acc aaa tct tct ttc tct gtt cgt tgt     148
Thr Leu Leu Pro Leu Pro Ser Thr Lys Ser Ser Phe Ser Val Arg Cys
        30                  35                  40 tct ctt cct cag cca tca aag cca cgc tct gga acc agc tct gtt cac     196
Ser Leu Pro Gln Pro Ser Lys Pro Arg Ser Gly Thr Ser Ser Val His
    45                  50                  55 gcc gtt atg aca ctc gcc atg g                                       218
Ala Val Met Thr Leu Ala Met
 60                  65

<210> SEQ ID NO 8
<211> LENGTH: 66
<212> TYPE: PRT
<213> ORGANISM: Arabidopsis thaliana

<400> SEQUENCE: 8

Met Arg Ser Ser Cys Cys Ser Ser Ala Ile Gly Gly Phe Phe Asp His
 1               5                  10                  15

Arg Arg Glu Leu Ser Thr Ser Thr Pro Ile Ser Thr Leu Leu Pro Leu
            20                  25                  30

Pro Ser Thr Lys Ser Ser Phe Ser Val Arg Cys Ser Leu Pro Gln Pro
        35                  40                  45

Ser Lys Pro Arg Ser Gly Thr Ser Ser Val His Ala Val Met Thr Leu
    50                  55                  60

Ala Met
 65

<210> SEQ ID NO 9
<211> LENGTH: 29
<212> TYPE: DNA
```

<213> ORGANISM: Artificial Sequence
<220> FEATURE:
<223> OTHER INFORMATION: Description of artificial sequence: primer
<220> FEATURE:
<221> NAME/KEY: primer_bind
<222> LOCATION: (1)..(29)

<400> SEQUENCE: 9
aagtcgacgc tgttacccaa gtgagaacg                                29

<210> SEQ ID NO 10
<211> LENGTH: 30
<212> TYPE: DNA
<213> ORGANISM: Artificial Sequence
<220> FEATURE:
<223> OTHER INFORMATION: Description of artificial sequence: primer
<220> FEATURE:
<221> NAME/KEY: primer_bind
<222> LOCATION: (1)..(30)

<400> SEQUENCE: 10
aacccgggtg gcttaagagg tttattatgg                               30

<210> SEQ ID NO 11
<211> LENGTH: 28
<212> TYPE: DNA
<213> ORGANISM: Artificial Sequence
<220> FEATURE:
<223> OTHER INFORMATION: Description of artificial sequence: primer
<220> FEATURE:
<221> NAME/KEY: primer_bind
<222> LOCATION: (1)..(28)

<400> SEQUENCE: 11
ggtaccggcg tcattgttga tgagatcg                                 28

<210> SEQ ID NO 12
<211> LENGTH: 24
<212> TYPE: DNA
<213> ORGANISM: Artificial Sequence
<220> FEATURE:
<223> OTHER INFORMATION: Description of artificial sequence: primer
<220> FEATURE:
<221> NAME/KEY: primer_bind
<222> LOCATION: (1)..(24)

<400> SEQUENCE: 12
ccatggtggc gagtgtcata acgg                                     24

<210> SEQ ID NO 13
<211> LENGTH: 27
<212> TYPE: DNA
<213> ORGANISM: Artificial Sequence
<220> FEATURE:
<221> NAME/KEY: primer_bind
<222> LOCATION: (1)..(27)
<220> FEATURE:
<223> OTHER INFORMATION: Description of artificial sequence: primer

<400> SEQUENCE: 13
gtcgactcaa tcgagacgac gtagaag                                  27

<210> SEQ ID NO 14
<211> LENGTH: 25
<212> TYPE: DNA
<213> ORGANISM: Artificial Sequence
<220> FEATURE:
<223> OTHER INFORMATION: Description of artificial sequence: primer
<220> FEATURE:

```
                              -continued
<221> NAME/KEY: primer_bind
<222> LOCATION: (1)..(25)

<400> SEQUENCE: 14
ccatgggcaa gagtcttcga atcgg                                    25
```

CHANGING THE FINE CHEMICAL CONTENT IN ORGANISMS BY GENETICALLY MODIFYING THE SHIKIMATE PATHWAY

RELATED APPLICATIONS

This application is the U.S. national phase (under 35 U.S.C. 371) of international application PCT/EP1/07391 filed 28 Jun. 2001 which designated the U.S. and which claims the benefit of German application 100 30 647.0 filed Jun. 29. 2000 and German application 100 64 454.6 filed Dec. 21. 2000.

The present invention relates to a process for the production of fine chemicals, in particular vitamin E, vitamin K and/or ubiquinone by culturing organisms, in particular plants, whose shikimate pathway is genetically modified over that of the wild type, and to the transgenic organisms themselves.

Organisms, in particular plants, exhibit a series of metabolites which are of high economical importance as fine chemicals. Fine chemicals which may be mentioned by way of example are aromatic amino acids, salicylic acid derivatives, phenylpropanoids, flavonoids, stilbenes, xanthones and quinones, in particular the mixed prenyl lipid compounds with vitamin E or vitamin K activity.

Using biotechnological processes for the production of fine chemicals, organisms which are capable of producing these fine chemicals are cultured and the desired fine chemicals are isolated from the organisms.

It is desirable for economical processes for the biotechnological production of fine chemicals, but also for the use of the organisms as processed or unprocessed foodstuffs or feedstuffs, to modify the fine chemical content in the organisms in a directed fashion, such as, for example, to increase the content of the desired fine chemical and/or to inhibit the metabolite flux toward undesired fine chemicals.

Examples of economically important fine chemicals are plastoquinones, ubiquinones and compounds with vitamin E or vitamin K activity which exhibit an isoprenoid side chain linked to an aromatic nucleus.

The naturally occurring eight compounds with vitamin E activity are derivatives of 6-chromanol (Ullmann's Encyclopedia of Industrial Chemistry, Vol. A 27 (1996), VCH Verlagsgesellschaft, Chapter 4, 478-488, Vitamin E). The tocopherol group (1a-d) exhibits a saturated side chain, while the tocotrienol group (2a-d) exhibits an unsaturated side chain:

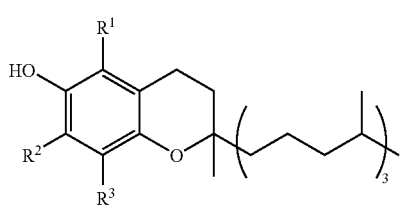

(1)

1a, α-tocopherol: $R^1=R^2=R^3=CH_3$
1b, β-tocopherol: $R^1=R^3=CH_3$, $R^2=H$
1c, γ-tocopherol: $R^1=H$, $R^2=R^3=CH_3$
1d, δ-tocopherol: $R^1=R^2=H$, $R^3=CH_3$

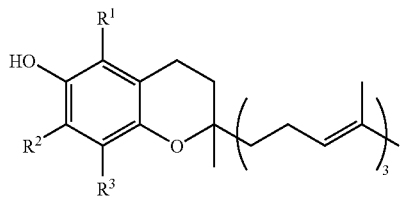

(2)

2a, α-tocotrienol: $R^1=R^2=R^3=CH_3$
2b, β-tocotrienol: $R^1=R^3=CH_3$, $R^2=H$
2c, γ-tocotrienol: $R^1=H$, $R^2=R^3=CH_3$
2d, δ-tocotrienol: $R^1=R^2=H$, $R^3=CH_3$ Within the present invention, vitamin E is understood to include all the abovementioned tocopherols and tocotrienols with vitamin E activity.

These compounds with vitamin E activity are important natural lipid-soluble antioxidants. Vitamin E deficiency leads to pathophysiological situations in humans and animals. Thus, vitamin E compounds are of great economic value as additives in the food and feed sector, in pharmaceutical formulations and in cosmetic applications.

The naturally occurring compounds with vitamin K activity are derivatives of 1,4-naphthoquinone (Ullmann's Encyclopedia of Industrial Chemistry, Vol. A 27 (1996), VCH Verlagsgesellschaft, Chapter 5, 488-506, vitamin K). Phylloquinone (earlier name: vitamin $K_1$) exhibits a largely saturated side chain, while the group of the menaquinones (earlier name: vitamin $K_2$) exhibit an unsaturated side chain with 4 to 13 isoprenyl residues.

Within the present invention, vitamin K is understood as including all compounds with vitamin K activity, in particular the abovementioned compounds.

The starting point of the isoprenoid side chain biosynthesis is isopentenyl pyrophosphate (IPP). IPP is in equilibrium with its isomer dimethylallyl pyrophosphate (DMAPP). Condensation of IPP with DMAPP head to tail results in the monoterpene ($C_{10}$) geranyl pyrophosphate (GPP). Addition of further IPP units results in the sesquiterpene ($C_{15}$) farnesyl pyrophosphate (FPP) and in the diterpene ($C_{20}$) geranylgeranyl pyrophosphate (GGPP).

Phylloquinone contains a $C_{20}$ phytyl chain, in which only the first isoprene unit contains a double bond. GGPP is transformed into phytyl pyrophosphate (PPP), the starting material for the further formation of tocopherols, by geranylgeranyl pyrophosphate oxidoreductase (GGPPOR).

The ring structures of the mixed prenyl lipids which lead to the formation of vitamin E and K are quinones whose starting metabolites are derived from the shikimate pathway.

Chorismate is formed starting from erythrose-4-phosphate and phosphoenolpyruvate (PEP) by the condensation of these via the intermediates 3'-dehydroquinate, 3'-dehydroshikimate, shikimate, shikimate-3-phosphate and 5'-enolpyruvylshikimate-3-phosphate to give 3-deoxy-D-arabino-heptulosonate-7-phosphate (DAHP). Erythrose-4-phosphate is formed in the Calvin cycle, while PEP is provided by glycolysis.

In higher plants, tyrosine is formed starting from chorismate via prephenate and arogenate. The aromatic amino acid tyrosine is converted into hydroxyphenylpyruvate, which is converted into homogentisic acid by dioxygenation.

Homogentisic acid is subsequently bound to phytyl pyrophosphate (PPP) or geranylgeranyl pyrophosphate to form the precursors of α-tocopherol and α-tocotrienol, namely 2-methyl-6-phytyl-hydroquinone and 2-methyl-6-geranylgeranylhydroquinone, respectively. Methylation steps with S-adenosylmethionine as methyl group donor first lead to 2,3-dimethyl-6-phytylquinol, subsequent cyclization leads to γ-tocopherol, and further methylation to α-tocopherol.

It is known to modify the vitamin E content in plants by overexpressing or down-regulating biosynthesis genes of the tocopherol synthetic pathway, which is understood as meaning, for the purposes of the present invention, the biosynthetic pathway from hydroxyphenolpyruvate through tocopherol.

WO 97/27285 describes a modification of the tocopherol content by increased expression or by down-regulation of the enzyme p-hydroxyphenylpyruvate dioxygenase (HPPD).

WO 99/04622 and D. DellaPenna et al., Science 1998, 282, 2098-2100 describe gene sequences encoding a γ-tocopherol methyltransferase from Synechocystis PCC6803 and *Arabidopsis thaliana* and its incorporation into transgenic plants with a modified vitamin E content.

It is furthermore known to modify the vitamin E content in plants by overexpressing or down-regulating biosynthesis genes of the biosynthetic pathway of the isoprenoid side chain.

WO 99/23231 shows that the expression of a geranylgeranyl reductase in transgenic plants results in an increased tocopherol biosynthesis.

WO 00/08169 describes gene sequences encoding a 1-deoxy-D-xylose-5-phosphate synthase and a geranylgeranyl pyrophosphate oxidoreductase and their incorporation into transgenic plants with a modified vitamin E content.

While all these methods yield organisms, in particular plants, with a modified content of the fine chemical vitamin E, the level of the vitamin E content is still frequently unsatisfactory for processes for the production of vitamin E by isolation from the transgenic organisms.

It is an object of the present invention to provide a further process for the production of fine chemicals by culturing organisms, or transgenic organisms which are capable of producing fine chemicals, with optimized properties which do not exhibit the above-described shortcomings of the prior art.

We have found that this object is achieved by a process for the production of fine chemicals in which organisms are cultured whose shikimate pathway is genetically modified over that of the wild type.

Shikimate pathway is to be understood as meaning for the purposes of the present invention, in particular for higher plants, the above-described biosynthetic pathway starting from D-erythrose-4-phosphate via shikimate, chorismate, prephenate, arogenate, tyrosine up to and including 4-hydroxyphenylpyruvate (G. Michal, Biochemical Pathways, Biochemie-Atlas, Spektrum Akademischer Verlag Heidelberg, Berlin, 1999, pages 59 to 60, FIGS. 4. 7-1 and Chapter 4.7.1).

Preferably, shikimate pathway is to be understood as meaning for the purposes of the present invention the metabolic pathway from shikimate to 4-hydroxyphenylpyruvate, especially preferably the metabolic pathway from chorismate to 4-hydroxyphenylpyruvate, the metabolic pathway for plants proceeding from chorismate via prephenate, arogenate and tyrosine.

Fine chemicals are to be understood as meaning metabolic products of the organism which result from the shikimate pathway. In this context, the shikimate pathway starts with D-erythrose-4-phosphate and ends with 4-hydroxyphenylpyruvate, as described above. For these metabolites, the starting compound D-erythrose-4-phosphate, the end product 4-hydroxyphenylpyruvate, and all the abovementioned intermediates of the shikimate pathway constitute the starting compounds, hereinbelow also termed intermediates, which are biotransformed by the organism into the metabolites.

Preferred fine chemicals are the aromatic amino acids, such as, for example, phenylalanine, tyrosine and tryptophan, salicylic acid derivatives, folic acid derivatives, phenylpropanoids, such as, for example, lignin, lignans or coumarins, in particular scopoletin or scopolin, flavonoids such as, for example, chalcones, flavanones, flavanols, anthocyanidins or isoflavonoids, stilbenes, xanthones or quinone derivatives such as, for example, vitamin E, vitamin K, ubiquinones, plastoquinones or shikonin.

Especially preferred fine chemicals are vitamin E, vitamin K or ubiquinone, in particular vitamin E.

Depending on whether the genetic modification of the shikimate pathway leads to an increase or reduction of the metabolite flux toward a certain intermediate, which forms part of the shikimate pathway, the content of the fine chemical which is biosynthesized in the organism from this intermediate is increased or reduced. Thus, genetic modification of the shikimate pathway is preferably understood as meaning the increase or reduction of the metabolite flux toward an intermediate of the shikimate pathway.

Genetic modifications of the shikimate pathway which lead to an increased metabolite flux toward an intermediate and thus of the corresponding fine chemical are, for example, the following measures A, B or C:

A: Increased activity of at least one enzyme of the shikimate pathway of the wild type,
for example by overexpressing genes of the shikimate pathway which encode proteins with this enzymatic activity by switching off negative regulatory mechanisms of metabolic pathways leading to the intermediate, such as, for example, switching off the feedback inhibition or introduction of orthologous genes which are not subject to regulation in the desired organism.

B: Introduction into the organism of at least one gene to which no orthologous gene exists in the wild type and which bridges the metabolic pathway of the shikimate pathway of the wild type. For example, this gene may cause, owing to the new gene function, an increased substance flux toward the intermediate where bridging ends.

C: Inactivation of genes which encode enzymes which compete with the enzymes of the metabolic pathway leading to the desired product.
Genetic modifications of the shikimate pathway which lead to a reduced metabolite flux toward an intermediate and thus of the corresponding fine chemical are, for example, the following measures D, E, or F:

D: Overexpression of a metabolic gene, and thus an increase in the corresponding enzyme activity which leads away from this intermediate;

E: Inactivation of genes which encode enzymes leading to this intermediate, for example by antisense technology or cosuppression;

F: Expression of a gene to which no orthologous gene exists in the wild type. For example, this gene can bridge the metabolic pathway of the shikimate pathway of the wild type and, owing to the new gene function, can cause a reduced substance flux toward the bridged intermediates.

In a preferred embodiment of the process according to the invention, the genetic modification of the shikimate pathway in the organism leads to an increased metabolite flux toward a desired intermediate and thus to an increase in the corresponding desired fine chemical.

It is preferred to increase the metabolite flux toward a desired intermediate of the shikimate pathway and thus to the desired fine chemical by at least one measure selected from the group of measures A and B, that is to say by measure A and/or B, measures A and B having the above-described meanings.

Thus, a preferred embodiment of the process according to the invention comprises carrying out at least one measure selected from the group of measures A and B for genetically modifying the shikimate pathway, A and B having the following meanings:

A: increasing the activity of at least one enzyme of the shikimate pathway of the wild type;
B: introducing at least one gene into the organism, to which no orthologous gene exists in the wild type and which bridges the metabolic pathway of the shikimate pathway of the wild type.

Increasing the activity of at least one enzyme of the shikimate pathway of the wild type in accordance with measure A can be effected, for example, by overexpressing nucleic acids, i.e. genes of the shikimate pathway, which encode, proteins with this enzymatic activity, by switching off negative regulatory mechanisms of metabolic pathways leading to the intermediate, such as, for example, switching off feedback inhibition, or introducing orthologous genes which are not subject to regulation in the desired organism.

Preferably, the activity of at least one enzyme of the shikimate pathway of the wild type is increased in accordance with measure A by overexpressing nucleic acids of the shikimate pathway which encode proteins with this enzymatic activity.

In a preferred embodiment of the process, measure A is carried out by introducing, into the organism, a nucleic acid encoding a chorismate mutase.

A chorismate mutase is to be understood as meaning a protein which has the enzymatic activity of converting chorismate into prephenate.

In principle, all chorismate mutases can be used in the process according to the invention such as, for example, the *Petroselinum Crispum* chorismate mutase (accession number: T14902, T14901), *Streptomyces coelicolor* chorismate mutase (T36865), *Bacillus subtilis* chorismate mutase (A33894), *Aspergillus nidulans* chorismate mutase (AAD30065), or the *Arabidopsis thaliana* chorismate mutases described hereinbelow or the chorismate mutase activity of *E. coli* chorismate mutase-prephenate dehydrogenase (tyrA) described hereinbelow.

In a preferred embodiment, chorismate mutase genes are used which encode a chorismate mutase whose activity is subject to reduced post-translational regulation in the organism. Reduced regulation is to be understood as meaning not more than 99% regulation of the activity, preferably not more than 70%, especially preferably 50%, particularly preferably 0%, i.e. no regulation of the activity, compared with the wild-type regulation.

Chorismate mutase genes which encode a chorismate mutase whose activity in the organism is subject to reduced, in particular no, regulation, are, for example, chorismate mutase genes from organisms from different genera or chorismate mutase genes from the same organism or organisms of related genera which are subject to reduced, in particular no, post-translational regulation at the localization of expression.

Organisms are to be understood as meaning in accordance with the invention prokaryotic organisms or eukaryotic organisms such as, for example, bacteria, yeasts, algae, mosses, fungi or plants which are capable, as the wild type or by genetic modification, of producing the abovementioned fine chemicals. Preferred organisms are photosynthetically active organisms such as, for example, *cyanobacteria*, mosses, algae or plants which are already capable of the wild type of producing the abovementioned fine chemicals.

Especially preferred organisms are plants.

In a further preferred embodiment of measure A of the process according to the invention, chorismate mutase genes which encode a chorismate mutase whose activity is subject, in plants, to reduced post-translational regulation, are introduced into lants.

They are, for example, some bacterial chorismate mutase genes or chorismate mutase genes derived therefrom, i.e. nucleic acids which encode a protein comprising the amino acid sequence of a bacterial chorismate mutase whose activity is subject, in plants, to reduced post-translational activity, for example the nucleic acid described hereinbelow encoding the chorismate mutase activity of the *E. coli* chorismate mutase-prephenate dehydrogenase (tyrA) or a sequence derived from this sequence by substitution, insertion or deletion of amino acids, which has at least 30% homology, preferably at least 50% homology, more referably at least 70% homology, especially preferably at least 90% homology at the amino acid level with the sequence of the bacterial chorismate mutase and which has the enzymatic property of a chorismate mutase.

The term "substitution" is to be understood as meaning, in the description, the exchange of one or more amino acids by one or more amino acids. It is preferred to carry out so-called conservative exchanges in which the replaced amino acid has a similar property as the original amino acid, for example the exchange of Glu for Asp, Gln for Asn, Val for Ile, Leu for Ile and Ser for Thr.

Deletion is the replacement of an amino acid by a direct bond. Preferred positions for deletion of the termino of the polypeptide and the linkages between the individual protein domains.

Insertions are introductions of amino acids into the polypeptide chain, a direct bond formally being replaced by one or more amino acids.

Homology between two proteins is preferably understood as meaning the identity of the amino acids over in each case the entire length of the protein which is preferably calculated by comparison with the aid of the program algorithm GAP(UWGCG, University of Wisconsin, Genetic Computer Group) setting the following parameters:

Gap Weight: 12
Length Weight: 4
Average Match: 2.912
Average Mismatch: −2.003

Accordingly, a protein which has at least 30% homology at the amino acid level with the sequence of the above-described *E. coli* chorismate mutase is to be understood as meaning a protein which, upon comparison of its sequence with the sequence of the above-described chorismate mutase, preferably using the above program algorithm with the above parameter set, has at least 30% homology.

The bacterial chorismate mutase genes or the chorismate mutase genes derived therefrom may also encode proteins which have the property of a chorismate mutase and the property of a further enzyme, such as, for example, the chorismate mutase-prephenate dehydrogenase gene (tyrA) from *E. coli* K12, which is described hereinbelow. As described hereinbelow, this embodiment is especially preferred when carrying out measures A and B in combination.

In an especially preferred embodiment of measure A of the process according to the invention, in particular when carrying out measure A alone, the chorismate mutase genes are introduced into specific sites in the organism at which the corresponding chorismate mutases are subject to reduced post-translational regulation.

In this context, it is preferred to use nucleic acids encoding a chorismate mutase from the same organism or from organisms of related genera which are subject to reduced post-translational regulation at the site of expression.

The isoforms of chorismate mutases isolated from different compartments of an organism differ with regard to their regulation.

The corresponding chorismate mutase genes from a specific compartment of the organism or from organisms of related genera can be introduced into other compartments of the organism in which the encoded chorismate mutases are not subject to post-translational regulation.

In an especially preferred embodiment of the process according to the invention in plants, a nucleic acid encoding a plant cytosolic chorismate mutase is introduced into plastids of plants in order to carry out measure A.

Nucleic acids which are suitable for this purpose in principle are all nucleic acids which encode a plant cytosolic chorismate mutase, preferably the nucleic acid encoding an *Arabidopsis thaliana* cytosolic chorismate mutase (Seq ID No. 3) and natural or unnatural nucleic acids derived therefrom.

It has been found that, in various organisms, chorismate mutase exists in various isoforms. Thus, three different chorismate utases were isolated from *Arabidopsis thaliana* (Eberhard et al. 1993. FEBS 334, 233-236; Eberhard et al. 1996. Plant J. 10, 815-821; Mobley et al. 1999.Gene 15;240 (1):115-123).

These isoforms differ from each other with regard to their localization and their enzymatic properties. Thus, chorismate mutase-1 is localized in the plastids and is regulated allosterically by the aromatic amino acids.

The cytosolic isoenzyme chorismate mutase-2 is subject to no known regulation (Benesova, M. Bode, R, Phytochemistry 1992, 31, 2983-2987).

Nucleic acids encoding an *Arabidopsis thaliana* cytosolic chorismate mutase and natural or unnatural nucleic acids derived therefrom are to be understood as meaning nucleic acids which encode a protein comprising the amino acid sequence of cytosolic chorismate mutase (SEQ ID No. 4) or a sequence derived from this sequence by substitution, insertion or deletion of amino acids which has at least 30% homology, preferably at least 50% homology, more preferably at least 70% homology, especially preferably at least 90% homology at the amino acid level with sequence SEQ ID No. 4 and which has the enzymatic property of a chorismate mutase.

A protein which has at least 30% homology at the amino acid level with sequence SEQ ID No. 4 is to be understood, accordingly, as meaning a protein which, upon comparison of its sequence with sequence SEQ ID No. 4, preferably using the above program algorithm with the above parameter set, has at least 30% homology.

In another preferred embodiment of the process according to the invention, a nucleic acid encoding the *Arabidopsis thaliana* cytosolic chorismate mutase (SEQ ID No. 4) is introduced into plastids of plants.

Suitable nucleic acid sequences can be obtained for example by back translating the polypeptide sequence in accordance with the genetic code.

Codons which are preferably used for this purpose are those which are frequently used in accordance with the plant-specific codon usage. The codon usage can be determined readily with reference to computer evaluations of other, known genes of the plant in question.

In a further especially preferred embodiment of the process according to the invention, a nucleic acid of the sequence SEQ ID No. 3 is introduced into plastids of plants. Sequence SEQ ID No. 3 represents the gene of the *Arabidopsis thaliana* cytosolic chorismate mutase (chorismate mutase-2).

The introduction, into plastids of plants, of nucleic acids encoding a chorismate mutase can be achieved for example as described in detail hereinbelow for chorismate mutase prephenate dehydrogenase by introducing, into plants, expression cassettes whose nucleic acid sequence encodes a chorismate mutase fusion protein, part of the fusion protein being a transit peptide which governs translocation of the polypeptide. Preferred are chloroplast-specific transit peptides which are cleaved off enzymatically from the chorismate mutase portion after translocation of the cytosolic chorismate mutase into the chloroplasts.

In a further especially preferred embodiment of the process according to the invention, a nucleic acid construct comprising a nucleic acid encoding a plastid transit peptide and a nucleic acid which encodes a protein comprising the amino acid sequence SEQ ID No. 4 or a sequence derived from this sequence by substitution, insertion or deletion of amino acids which has at least 30% homology at the.amino acid level with sequence SEQ ID No. 2 and which has the enzymatic property of a chorismate mutase is introduced into the plant.

Nucleic acids encoding plastid transit peptides are, for example, DNA sequences of three cassettes of the plastid transit peptide of the tobacco plastid transketolase in three reading frames as KpnI/BamHI fragments with an ATG codon in the NcoI cleavage site:

```
pTP09
KpnI_GGTACCATGGCGTCTTCTTCTTCTCTCACTCTCTCTCAAGCTATC

CTCTCTCGTTCTGTCCCTCGCCATGGCTCTGCCTCTTCTTCTCAACTTTC

CCCTTCTTCTCTCACTTTTTCCGGCCTTAAATCCAATCCCAATATCACCA

CCTCCCGCCGCCGTACTCCTTCCTCCGCCGCCGCCGCCGCCGTCGTAAGG

TCACCGGCGATTCGTGCCTCAGCTGCAACCGAAACCATAGAGAAAACTGA

GACTGCGGGATCC_BamHI pTP10
KpnI_GGTACCATGGCGTCTTCTTCTTCTCTCACTCTCTCTCAAGCTATC

CTCTCTCGTTCTGTCCCTCGCCATGGCTCTGCCTCTTCTTCTCAACTTTC

CCCTTCTTCTCTCACTTTTTCCGGCCTTAAATCCAATCCCAATATCACCA

CCTCCCGCCGCCGTACTCCTTCCTCCGCCGCCGCCGCCGCCGTCGTAAGG

TCACCGGCGATTCGTGCCTCAGCTGCAACCGAAACCATAGAGAAAACTGA

GACTGCGCTGGATCC_BamHI
```

```
pTP11
KpnI_GGTACCATGGCGTCTTCTTCTTCTCTCACTCTCTCTCAAGCTATC

CTCTCTCGTTCTGTCCCTCGCCATGGCTCTGCCTCTTCTTCTCAACTTTC

CCCTTCTTCTCTCACTTTTTCCGGCCTTAAATCCAATCCCAATATCACCA

CCTCCCGCCGCCGTACTCCTTCCTCCGCCGCCGCCGCCGCCGTCGTAAGG

TCACCGGCGATTCGTGCCTCAGCTGCAACCGAAACCATAGAGAAAACTGA

GACTGCGGGGATCC_BamHI,
``` or the nucleic acid encoding the plastid transit peptide of the *Arabidopsis thaliana* plastid chorismate mutase-1 (SEQ ID No. 7):

```
KpnI_GGCGTCATTGTTGATGAGATCGTCTTGTTGCTCCTCTGCGATTGG

TGGGTTCTTCGACCATCGACGTGAATTATCAACCTCAACACCCATTTCCA

CTCTTCTTCCTCTTCCATCAACCAAATCTTCTTTCTCTGTTCGTTGTTCT

CTTCCTCAGCCATCAAAGCCACGCTCTGGAACCAGCTCTGTTCACGCCGT

TATGACACTCG_NCol
```

The nucleic acid encoding the plastid transit peptide of the *Arabidopsis thaliana* plastid chorismate mutase-1 is preferably used for the localization of a cytosolic chorismate mutase in plastids.

In a further especially preferred embodiment of the process according to the invention, a nucleic acid construct comprising a nucleic acid encoding a plastid transit peptide of the *Arabidopsis thaliana* plastid chorismate mutase-1 and a nucleic acid which encodes a protein comprising the amino acid sequence SEQ ID No. 4 or a sequence derived from this sequence by substitution, insertion or deletion of amino acids, which has at least 30% homology at the amino acid level with sequence SEQ ID No. 4 and which has the enzymatic property of a chorismate mutase is therefore introduced into the plant.

It is especially preferred for measure A of the process according to the invention to introduce, into plants, a nucleic acid construct comprising the sequence (SEQ ID No. 5).

SEQ ID No. 5 constitutes a nucleic acid construct of the nucleic acid encoding the plastid transit peptide of the *Arabidopsis thaliana* plastid chorismate mutase-1 and the nucleic acid encoding the *Arabidopsis thaliana* cytosolic chorismate mutase-2.

The present application relates in particular to these nucleic acid constructs and to their use in measure A of the process according to the invention.

FIG. 1 shows by way of example the biosynthetic scheme starting from erythrose-4-phosphate to vitamin E. Owing to the additional expression of a chorismate mutase gene, the shikimate pathway of the wild type is genetically modified and the metabolite flux toward hydroxyphenylpyruvate is increased. The hydroxyphenylpyruvate, of which greater quantities are now available, is reacted further toward tocopherols. An elevated hydroxyphenylpyruvate content leads to an elevated conversion toward vitamin E and/or vitamin K. An elevated hydroxyphenylpyruvate content preferably leads to an increased vitamin E content.

An expression cassette is generated as described in detail hereinbelow by fusing a suitable promoter with a suitable chorismate mutase nucleic acid sequence and a nucleic acid preferably inserted between promoter and chorismate mutase nucleic acid sequence which encodes a plastid transit peptide, i.e. preferably by fusing a suitable promoter with a suitable above-described nucleic acid construct, and with a polyadenylation signal, using customary recombination and cloning techniques as they are described, for example, by T. Maniatis, E. F. Fritsch and J. Sambrook, Molecular Cloning: A Laboratory Manual, Cold Spring Harbor Laboratory, Cold Spring Harbor, N.Y. (1989) and by T. J. Silhavy, M. L. Berman and L. W. Enquist, Experiments with Gene Fusions, Cold Spring Harbor Laboratory, Cold Spring Harbor, N.Y. (1984) and by Ausubel, F. M. et al., Current Protocols in Molecular Biology, Greene Publishing Assoc. and Wiley-Interscience (1987).

Measure B for modifying the shikimate pathway of the wild type is carried out as described hereinabove by introducing, into the organism, at least one gene for which no orthologous gene exists in the wild type and which bridges the metabolic pathway of the shikimate pathway of the wild type. This gene encodes an enzyme which, owing to the new enzymatic activity, brings about an increased substance flux towards the intermediate where the bridging ends. This novel enzymatic activity is preferably subject to no regulation by the organism, that is to say short-circuits the metabolic pathway in order to circumvent, for example, limiting regulatory positions in the metabolism. This makes it possible to uncouple the metabolite flux toward limiting substances from existing regulations.

A gene which is orthologous to the wild type is to be understood as meaning a gene which is derived from another organism, the enzyme activity which the gene encodes already being present in the wild type.

Accordingly, the formulation "gene to which no orthologous gene exists in the wild type" is to be understood as meaning a gene from another organism, the enzyme activity which the gene encodes not having been present, or not having been activated, in the wild type prior to transformation.

A gene orthologous to the wild type is preferably understood as meaning a functional equivalent from another organism, functional equivalent being understood as meaning the totality of the properties of the gene product (protein).

Accordingly, the formulation "gene to which no orthologous gene exists in the wild type" is preferably understood as meaning a gene to which no functional equivalent in accordance with the above-mentioned definition exists in the wild type, thus establishing a metabolic performance which generates an alternative metabolic pathway in order to produce a product already present in the plant (metabolite contained).

Organisms are to be understood as meaning, in accordance with the invention as described hereinabove for measure A, prokaryotic organisms or eukaryotic organisms such as, for example, bacteria, yeasts, algae, mosses, fungi or plants which are capable of producing the abovementioned fine chemicals as the wild type or owing to genetic modification. Preferred organisms are photosynthetically active organisms such as, for example, cyano bacteria, mosses, algae or plants which are already capable as the wild type of producing the abovementioned fine chemicals.

Especially preferred organisms are plants.

In an especially preferred embodiment of the process according to the invention, plants are therefore used as the organisms to be transformed. In this case, genes to which no orthologous gene exists in the plant which are preferably suitable for carrying out measure B are bacterial genes.

In a preferred embodiment of measure B of the process according to the invention, the metabolic pathway of the shikimate pathway of the plant is bridged by the at least one gene which has been introduced.

In an especially preferred embodiment of measure B of the process according to the invention, a nucleic acid encoding a prephenate dehydrogenase is introduced into a plant. All genes which encode a prephenate dehydrogenase are suitable for the preferred embodiment of the process according to the invention.

A prephenate dehydrogenase is to be understood as meaning an enzyme which has the enzymatic activity of converting prephenate into 4-hydroxyphenylpyruvate.

Examples of nucleic acids which encode a prephenate dehydrogenase and which can be used in the process according to the invention are the prephenate dehydrogenase genes from *Lactococcus lactis* (accession X78413), Synechocystis spec PCC 6803 (slr2081), *Deinococcus radiodurans* (AAF10695) or *Bacillus subtilis* (P20692), all of which are known and accessible for example in Internet databases. Other examples can be found by homology alignments of the sequences with these known prephenate dehydrogenase genes, such as, for example, the potential prephenate dehydrogenase genes from *Termotoga maitima* (AAD35430) or *Heliobacter pylori* 26695 (accession AAD08422).

In a preferred embodiment of the process according to the invention using a prephenate dehydrogenase gene, a nucleic acid is introduced which encodes a protein comprising the amino acid sequence of the Synechocystis spec PCC 6803 prephenate dehydrogenase or a sequence derived from this sequence by substitution, insertion or deletion of amino acids which has at least 30% homology, preferably at least 50% homology, more preferably at least 70% homology, especially preferably at least 90% homology at the amino acid level with the sequence of the Synechocystis spec PCC 6803 prephenate dehydrogenase and which has the enzymatic property of a prephenate dehydrogenase.

Accordingly, a protein which has at least 30% homology at the amino acid level with the sequence of the Synechocystis spec PCC 6803 prephenate dehydrogenase is to be understood as meaning a protein which, upon alignment of its sequence with the sequence of the Synechocystis spec PCC 6803 prephenate dehydrogenase, preferably using the above program algorithm with the above parameter set, shows at least 30% homology.

FIG. 1 shows by way of example the biosynthetic scheme starting from erythrose-4-phosphate to the tocopherols. Owing to the additional expression of a prephenate dehydrogenase gene, the shikimate pathway of the wild type is genetically modified and the metabolite flux toward hydroxyphenylpyruvate is increased. The hydroxyphenylpyruvate, of which greater quantities are now available, is reacted further toward tocopherols. An elevated hydroxyphenylpyruvate content leads to an elevated conversion toward vitamin E and/or vitamin K. An elevated hydroxyphenylpyruvate content preferably leads to an increased vitamin E content.

However, it is advantageous, if appropriate in combination with the bridging according to the invention of the metabolic pathway, to overexpress further enzymes of the shikimate pathway in order to achieve an increased metabolite flux toward the desired fine chemicals.

In a further, preferred embodiment of the process according to the invention, measures A and B are therefore carried out in combination.

In an especially preferred embodiment of this process variant according to the invention, a nucleic acid encoding a prephenate dehydrogenase is introduced into a plant in combination with a nucleic acid encoding a chorismate mutase.

For example, this combination can be effected by introducing two nucleic acids, each of which encodes an enzyme with the activity of a chorismate mutase and an enzyme with the activity of a prephenate dehydrogenase, respectively. For this embodiment, it is necessary to introduce, into the plant, two different nucleic acids, each of which encodes one of these enzymes.

In a particularly preferred embodiment of the process according to the invention, this combination is effected in one nucleic acid by introducing, into a plant, a nucleic acid encoding a chorismate mutase-prephenate dehydrogenase.

The chorismate mutase-prephenate dehydrogenase gene encodes a protein which has the enzymatic properties of both a chorismate mutase and a prephenate dehydrogenase. Thus, introducing a nucleic acid overexpresses an enzymatic activity, or introduces an enzymatic activity, which is subject to reduced post-translational regulation (chorismate mutase) and an enzymatic property (prephenate dehydrogenase) is newly introduced.

A chorismate mutase-prephenate dehydrogenase is to be understood as meaning an enzyme which has the enzymatic activity of converting chorismate into 4-hydroxyphenylpyruvate.

In a further, especially preferred embodiment of this process variant according to the invention, a nucleic acid is introduced which encodes a protein comprising the amino acid sequence SEQ ID No. 2 or a sequence derived from this sequence by substitution, insertion or deletion of amino acids which has at least 30% homology, preferably at least 50% homology, more preferably at least 70% homology, especially preferably at least 90% homology at the amino acid level with sequence SEQ ID No. 2 and has the enzymatic property of chorismate mutase-prephenate dehydrogenase.

The protein with the amino acid sequence SEQ ID No. 2 constitutes the *E. coli* K12 chorismate mutase-prephenate dehydrogenase (tyrA).

Accordingly, a protein which has at least 30% homology at the amino acid level with sequence SEQ ID No.2 is to be understood as meaning a protein which, upon alignment of its sequence with sequence SEQ ID No.2, preferably using the above program algorithm with the above parameter set, has at least 30% homology.

All the nucleic acids mentioned in the description can be, for example, an RNA, DNA or cDNA sequence.

Suitable nucleic acid sequences can be obtained as described above by back-translating the polypeptide sequence in accordance with the genetic code.

Codons which are preferably used for this purpose are those which are used frequently in accordance with the organism-specific codon usage. The codon usage can be readily determined with reference to computer evaluations of other, known genes of the organism in question.

If, for example, the protein is to be expressed in a plant, it is frequently advantageous to use the plant's codon usage for the back-translation.

Further preferred chorismate mutase-prephenate dehydrogenases or their coding nucleic acids are, in particular, nucleic acids of bacterial origin such as, for example, the chorismate mutase-prephenate dehydrogenase genes from Erwinia herbicola (accession X60420; this protein can also be converted into a onofunctional prephenate dehydrogenase by deleting a 109 Bp region at the 5' end and then used for example as described above as prephenate dehydrogenase) or *Bordetella bronchiseptica* (accession AAF01289) or can be identified readily from various organisms whose genomic sequence is known by homology alignment of the amino acid sequences or of the corresponding back-translated nucleic acid sequences from data bases with SEQ ID No. 2 or the other sequences described hereinabove, such as, for example, the potential chorismate mutase-prephenate dehydrogenase genes from *Methanococcus janaschii* (accession Q58029).

Especially preferably used nucleic acids encode a bacterial chorismate mutase prephenate dehydrogenase.

A nucleic acid which is especially preferably used has the sequence SEQ ID No. 1. This nucleic acid constitutes a prokaryotic *E. Coli* K12 genomic DNA which encodes the chorismate mutase-prephenate dehydrogenase of the sequence SEQ ID No. 2, also termed tyrA gene.

FIG. 1 shows by way of example the biosynthetic scheme starting from erythrose-4-phosphate to the tocopherols. Owing to the additional expression of a chorismate mutase-prephenate dehydrogenase gene, the shikimate pathway of the wild type is genetically modified and the metabolite flux toward hydroxyphenylpyruvate is increased. The hydroxyphenylpyruvate, of which greater quantities are now available, is reacted further toward tocopherols. An elevated hydroxyphenylpyruvate content leads to an elevated conversion toward vitamin E and/or vitamin K. An elevated hydroxyphenylpyruvate content preferably leads to an increased vitamin E content.

In the process according to the invention for the production of fine chemicals, the step in which the transgenic organisms are cultured is preferably followed by harvesting the organisms and isolating the fine chemicals from the organisms.

The organisms are harvested in a manner known per se to suit the organism in question. Microorganisms such as bacteria, mosses, yeasts and fungi or plant cells which are cultured in liquid nutrient media by fermentation can be separated for example by centrifugation, decanting or filtration. Plants are grown on nutrient substrates in a manner known per se and harvested accordingly.

The fine chemicals are isolated from the harvested biomass in a
  manner known per se, for example by extraction and, if appropriate, further chemical or physical purification processes such as, for example, precipitation methods, crystallography, thermal separation methods such as rectification processes, or physical separation methods such as, for example, chromatography.

For example, vitamin E is preferably isolated from oil-containing plants by chemical conversion and distillation from vegetable oils or from the steam distillates (deodorizer condensates)
  obtained in the deodorization of vegetable oils.
  Further methods of isolating vitamin E from deodorizer condensates are described, for example, in DE 31 26 110 A1, EP 171 009 A2, GB 2 145 079, EP 333 472 A2 and WO 94/05650.

The transgenic organisms, in particular plants, are preferably generated by transforming the starting organisms, in particular plants, with a nucleic acid construct which comprises the above-described nucleic acids, in particular the nucleic acids encoding a chorismate mutase, a prephenate dehydrogenase or a chorismate mutase-prephenate dehydrogenase or the above-described nucleic acid constructs, in particular the nucleic acid construct encoding a plastid transit peptide and a cytosolic chorismate mutase, these nucleic acids . . .

These nucleic acid constructs in which the coding nucleic acid sequence or the coding nucleic acid construct is or are linked functionally to one or more regulatory signals, which ensure transcription and translation in organisms, in particular in plants, are also referred to hereinbelow as expression cassettes.

Accordingly, the invention furthermore relates to nucleic acid constructs acting as expression cassette and comprising a nucleic acid described above, in particular the nucleic acid encoding a chorismate mutase, a prephenate dehydrogenase or a chorismate mutase-prephenate dehydrogenase or the above-described nucleic acid constructs, in particular the nucleic acid construct encoding a plastid transit peptide and a cytosolic chorismate mutase which are linked functionally to one or more regulatory signals ensuring transcription and translation in the host organism, in particular in plants.

The expression cassette preferably comprises a nucleic acid encoding a plastid transit peptide which ensures localization in plastids.

The expression cassettes comprise regulatory signals, also regulatory nucleic acid sequences, which govern the expression of the coding sequence in the host cell. In accordance with a preferred embodiment, an expression cassette comprises upstream, i.e. at the 5' end of the coding sequence, a promoter and downstream, i.e. at the 3' end, a polyadenylation signal and, if appropriate, further regulatory elements linked operably to the interposed coding sequence for at least one of the above-described genes. Operable linkage is to be understood as meaning the sequential arrangement of promoter, coding sequence, terminator and, if appropriate, other regulatory elements in such a way that each of the regulatory elements can fulfill its intended function when the coding sequence is expressed.

The following text describes the preferred nucleic acid constructs, plant expression cassettes and methods of generating transgenic plants by way of example.

The sequences preferred for operable linkage, but not limited thereto, are targeting sequences for ensuring subcellular localization in the apoplast, in the vacuol, in plastids, in the mitochondrion, in the endoplasmatic reticulum (ER), in the nucleus, in elaioplasts or in other compartments, and translation enhancers such as the tobacco mosaic virus 5' leader sequence (Gallie et al., Nucl. Acids Res. 15 (1987), 8693-8711).

Promoters of the expression cassettes which are suitable are, in principle, any promoter which is capable of governing the expression of foreign genes in plants. Preferably, use is made of, in particular, a plant promoter or a promoter derived from a plant virus. Especially preferred is the cauliflower mosaic virus CaMV 35S promoter (Franck et al., Cell 21 (1980), 285-294). As is known, this promoter comprises various recognition sequences for transcriptional effectors which, in their totality, lead to permanent and constitutive expression of the gene which has been inserted (Benfey et al., EMBO J. 8 (1989), 2195-2202).

The expression cassette can also comprise a chemically inducible promoter by means of which the expression of the exogenous tyrA gene in the plant can be governed at a particular point in time. Examples of such promoters which can be used are, i.a. the PRP1 promoter (Ward et al., Plant. Mol. Biol. 22 (1993), 361-366), a salicylic-acid-inducible promoter (WO 95/19443), a benzenesulfonamide-inducible promoter (EP-A 388186), a tetracyclin-inducible promoter (Gatz et al., (1992) Plant J. 2, 397-404), an abscisic-acid-inducible promoter (EP-A 335528) or an ethanol- or cyclohexanone-inducible promoter (WO 93/21334).

Furthermore, preferred promoters are, in particular, those which ensure expression in tissues or plant organs in which, for example, the biosynthesis of the fine chemicals in question, in particular vitamin E or its precursors, takes place. Promoters which must be mentioned in particular are those which ensure leaf-specific expression. Promoters which may be mentioned are the potato cytosolic FBPase promoter or the potato ST-LSI promoter (Stockhaus et al., EMBO J. 8 (1989), 2445-245).

A foreign protein was expressed stably up to 0.67% of the total soluble seed protein in the seeds of transgenic tobacco plants with the aid of a seed-specific promoter (Fiedler and Conrad, Bio/Technology 10 (1995), 1090-1094). Thus, the expression cassette can comprise, for example, a seed-specific promoter (preferably the phaseolin promoter (U.S. Pat. No. 5,504,200), the USP promoter (Baumlein, H. et al., Mol. Gen. Genet. (1991) 225 (3), 459-467), the LEB4 promoter (Fiedler and Conrad, 1995), the sucrose binding protein promoter (Zitat), the LEB4 signal peptide, the gene to be expressed and an ER retention signal.

An expression cassette is generated for example by fusing a suitable promoter to a suitable, above-described nucleic acid sequence, in particular the nucleic acid sequence encoding a chorismate mutase, a prephenate dehydrogenase or a chorismate mutase-prephenate dehydrogenase, and, preferably, a nucleic acid which is inserted between promoter and nucleic acid sequence and which encodes a chloroplast-specific transit peptide, and to a polyadenylation signal, using customary recombination and cloning techniques as they are described, for example by T. Maniatis, E. F. Fritsch and J. Sambrook, Molecular Cloning: A Laboratory Manual, Cold Spring Harbor Laboratory, Cold Spring Harbor, N.Y. (1989) and by T. J. Silhavy, M. L. Berman and L. W. Enquist, Experiments with Gene Fusions, Cold Spring Harbor Laboratory, Cold Spring Harbor, N.Y. (1984) and by Ausubel, F. M. et al., Current Protocols in Molecular Biology, Greene Publishing Assoc. and Wiley-Interscience (1987).

Inserted sequences which, as described above for chorismate mutase, ensure targeting into the plastids are particularly preferred.

It is also possible to use expression cassettes whose nucleic acid sequence encodes a fusion protein, in particular a chorismate mutase, prephenate dehydrogenase or chorismate mutase-prephenate dehydrogenase fusion protein, part of the fusion protein being a transit peptide which governs translocation of the polypeptide. Preferred are chloroplast-specific transit peptides, which are cleaved enzymatically from the protein moiety, in particular the chorismate mutase, prephenate dehydrogenase and/or chorismate mutase-prephenate dehydrogenase moiety, after the proteins, in particular chorismate mutase, prephenate dehydrogenase or chorismate mutase-prephenate dehydrogenase have been translocated into the chloroplasts. Especially preferred is the transit peptide which is derived from plastid *Nicotiana tabacum* transcetolase or another transit peptide (for example the Rubisco small subunit transit peptide, or the ferredoxin NADP oxidoreductase transit peptide and also the isopentenyl pyrophosphate isomerase-2 transit peptide) or its functional equivalent.

The use of the transit peptide of the plastid chorismate mutase or its coding nucleic acid is particularly preferred for using the cytosolic chorismate mutase or the nucleic acid encoding a cytosolic chorismate mutase as described above.

Especially preferred for the use according to the invention of the other nucleic acids according to the invention are DNA sequences of three cassettes of the plastid transit peptide of the tobacco plastid transcetolase in three reading frames as KpnI/BamHI fragments with an ATG codon in the NcoI cleavage site:

pTP09
KpnI_GGTACCATGGCGTCTTCTTCTTCTCTCACTCTCTCTCAAGCTATC

CTCTCTCGTTCTGTCCCTCGCCATGGCTCTGCCTCTTCTTCTCAACTTTC

CCCTTCTTCTCTCACTTTTTCCGGCCTTAAATCCAATCCCAATATCACCA

CCTCCCGCCGCCGTACTCCTTCCTCCGCCGCCGCCGCCGCCGTCGTAAGG

TCACCGGCGATTCGTGCCTCAGCTGCAACCGAAACCATAGAGAAAACTGA

GACTGCGGGATCC_BamHI pTP10
KpnI_GGTACCATGGCGTCTTCTTCTTCTCTCACTCTCTCTCAAGCTATC

CTCTCTCGTTCTGTCCCTCGCCATGGCTCTGCCTCTTCTTCTCAACTTTC

CCCTTCTTCTCTCACTTTTTCCGGCCTTAAATCCAATCCCAATATCACCA

CCTCCCGCCGCCGTACTCCTTCCTCCGCCGCCGCCGCCGCCGTCGTAAGG

TCACCGGCGATTCGTGCCTCAGCTGCAACCGAAACCATAGAGAAAACTGA

GACTGCGCTGGATCC_BamHI pTP11
KpnI_GGTACCATGGCGTCTTCTTCTTCTCTCACTCTCTCTCAAGCTATC

CTCTCTCGTTCTGTCCCTCGCCATGGCTCTGCCTCTTCTTCTCAACTTTC

CCCTTCTTCTCTCACTTTTTCCGGCCTTAAATCCAATCCCAATATCACCA

CCTCCCGCCGCCGTACTCCTTCCTCCGCCGCCGCCGCCGCCGTCGTAAGG

TCACCGGCGATTCGTGCCTCAGCTGCAACCGAAACCATAGAGAAAACTGA

GACTGCGGGGATCC_BamHI

Another example of plastid transit peptide is the transit peptide of the *Arabidopsis thaliana* plastid isopentyl pyrophosphate isomerase-2 (IPP-2).

The nucleic acids according to the invention, in particular the nucleic acids encoding a chorismate mutase, a prephenate dehydrogenase or a chorismate mutase-prephenate dehydrogenase, can be synthesized or obtained naturally or comprise a mixture of synthetic and natural nucleic acid constituents or else be composed of various heterologous gene segments of various organisms.

Preferred as described above are synthetic nucleotide sequences with codons which are preferred by plants. These codons which are preferred by plants can be determined from codons with the highest protein frequency which are expressed in most of the plant species of interest.

When preparing an expression cassette, various DNA fragments can be manipulated in order to obtain a nucleotide sequence which expediently reads in the correct direction and which is provided with a correct reading frame. To connect the DNA fragments to each other, adapters or linkers may be added to the fragments.

The promoter and terminator regions can expediently be provided, in the direction of transcription, with a linker or polylinker comprising one or more restriction sites for insertion of this sequence. As a rule, the linker has 1 to 10, in most cases 1 to 8, preferably 2 to 6, restriction sites. In general, the linker within the regulatory regions has a size of less than 100 bp, frequently less than 60 bp, but at least 5 bp. The promoter can be either native, or homologous, or else foreign, or heterologous, to the host plant. The expression cassette preferably comprises, in the 5'-3' direction of transcription, the promoter, a coding nucleic acid sequence or a nucleic acid construct, and a region for transcriptional termination. Various termination regions can be exchanged for one another as desired.

Furthermore, manipulations which provide suitable restriction cleavage sites or which eliminate excess DNA or restriction cleavage sites may be employed. In-vitro mutagenesis, primer repair, restriction or ligation may be used in cases where insertions, deletions or substitutions, such as, for example, transitions and transversions, are suitable.

Complementary ends of the fragments may be provided for ligation in the case of suitable manipulations such as, for example, restriction, chewing-back or filling up overhangs for blunt ends.

Preferred polyadenylation signals are plant polyadenylation signals, preferably those which correspond essentially to *Agrobacterium tumefaciens* T-DNA polyadenylation signals, in particular those of gene 3 of the T-DNA (octopine synthase) of the Ti plasmid pTiACH5 (Gielen et al., EMBO J. 3 (1984), 835 et seq.) or functional equivalents.

The invention furthermore relates to the use of the above-described nucleic acids, in particular the nucleic acids encoding a chorismate mutase, a prephenate dehydrogenase or a chorismate mutase-prephenate dehydrogenase or of the above-described nucleic acid constructs or proteins, in particular the chorismate mutases, the prephenate dehydrogenases or the chorismate mutase-prephenate dehydrogenases for the generation of transgenic plants.

Preferably, the content of fine chemicals of these transgenic plants, in particular ubiquinone, vitamin E and/or vitamin K, preferably vitamin E, is increased over that of the wild type.

It is known that plants with a high vitamin E content have an increased resistance to abiotic stress. Abiotic stress is to be understood as meaning, for example, low temperatures, frost, drought, high temperatures and salt.

The invention therefore furthermore relates to the use of the above-mentioned nucleic acids for generating transgenic plants whose resistance to abiotic stress is increased over that of the wild type.

The above-described proteins and nucleic acids can be used for producing fine chemicals in transgenic organisms, preferably for producing vitamin E, vitamin K and/or ubiquinone, in particular vitamin E, in transgenic plants.

The transfer of foreign genes into the genome of an organism, in particular a plant, is termed transformation. In plants, in particular, methods known per se for transforming and regenerating plants from plant tissues or plant cells can be used for transient or stable transformation.

Suitable methods for the transformation of plants are protoplast transformation by polyethylene-glycol-induced DNA uptake, the biolistic method using the gene gun—the so-called particle bombardment method, electroporation, the incubation of dry embryos in DNA-containing solution, microinjection and the above-described *agrobacterium*-mediated gene transfer. The abovementioned methods are described, for example, in B. Jenes et al., Techniques for Gene Transfer, in: Transgenic Plants, Vol. 1, Engineering and Utilization, edited by S. D. Kung and R. Wu, Academic Press (1993), 128-143 and in Potrykus, Annu. Rev. Plant Physiol. Plant Molec. Biol. 42 (1991), 205-225).

The construct to be expressed is preferably cloned into a vector which is suitable for transforming *Agrobacterium tumefaciens*, for example pBin19 (Bevan et al., Nucl. Acids Res. 12 (1984), 8711).

Accordingly, the invention furthermore relates to vectors comprising the above described nucleic acids, nucleic acid constructs or expression cassettes.

Agrobacteria transformed with an expression cassette can be used in the known manner for transforming plants, for example by bathing scarified leaves or leaf sections in an agrobacterial solution and subsequently culturing them in suitable media.

The expression cassette can be employed not only in plants, but also for transforming bacteria, in particular *cyanobacteria*, mosses, yeasts, *filamentose* fungi and algae.

For the preferred generation of genetically modified plants, hereinbelow also termed transgenic plants, the fused expression cassette which encodes a protein according to the invention, in particular a chorismate mutase, prephenate dehydrogenase or a chorismate mutase-prephenate dehydrogenase, is preferably cloned into a vector, for example pBin19, which is suitable for transforming *Agrobacterium tumefaciens*.

Agrobacteria transformed with such a vector can then be used in the known manner for transforming plants, in particular cultured plants, for example by bathing scarified leaves or leaf sections in an agrobacterial solution and subsequently culturing them in suitable media.

The transformation of plants with agrobacteria is known, inter alia, from F. F. White, Vectors for Gene Transfer in Higher Plants; in Transgenic Plants, Vol. 1, Engineering and Utilization, edited by S. D. Kung and R. Wu, Academic Press, 1993, pp. 15-38. Transgenic plants which comprise, integrated into the expression cassette, a gene for the expression of a gene according to the invention, in particular a nucleic acid encoding a chorismate mutase, a prephenate dehydrogenase or a chorismate mutase-prephenate dehydrogenase, can be regenerated in the known manner from the transformed cells of the scarified leaves or leaf sections.

To transform a host plant with a nucleic acid encoding a chorismate mutase, prephenate dehydrogenase or chorismate mutase-prephenate dehydrogenase, an expression cassette is incorporated, as insertion, into a recombinant vector whose vector DNA comprises additional functional regulatory signals, for example sequences for replication or integration. Suitable vectors are described, inter alia, in "Methods in Plant Molecular Biology and Biotechnology" (CRC Press), Chapter 6/7, pp. 71-119 (1993).

Figure 2:
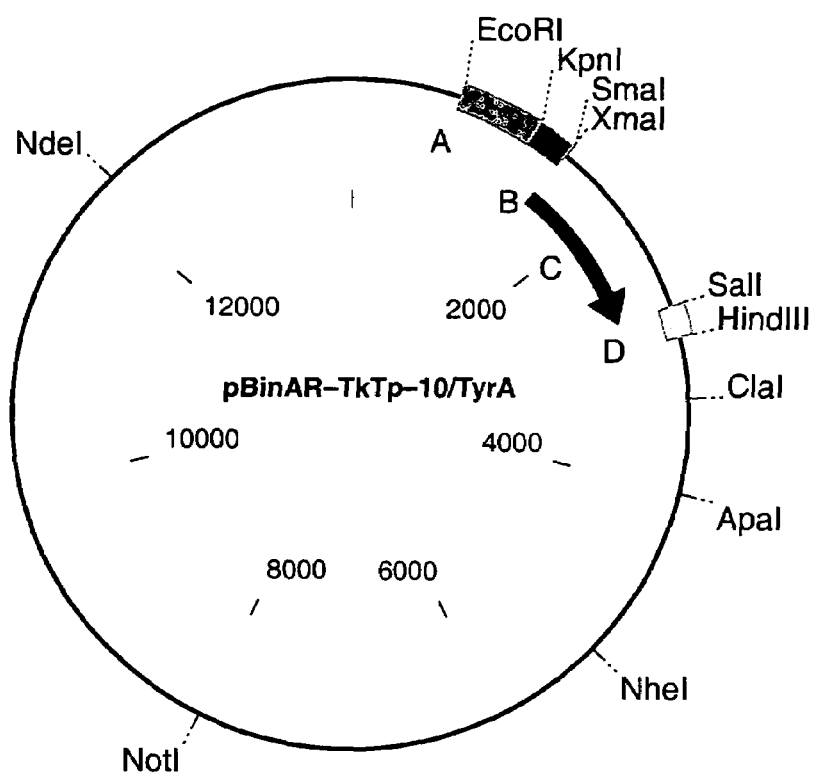

For example, the plant expression cassette can be incorporated into a derivative of the transformation vector pBin-19 with 35S promoter (Bevan, M., Nucleic Acids Research 12: 8711-8721 (1984)). FIG. 2 shows a derivative of the transformation vector pBin-19 with the seed-specific legumin B4 promoter.

Using the above-cited recombination and cloning techniques, the expression cassettes can be cloned into suitable vectors which allow their replication, for example in *E. coli*. Examples of suitable cloning vectors are pBR332, pUC series, M13mp series and pACYC184. Binary vectors, which are capable of replicating both in *E. coli* and in agrobacteria, are especially suitable.

The invention therefore relates to the use of the above-described nucleic acids, in particular the nucleic acids encoding a chorismate mutase, prephenate dehydrogenase or a chorismate mutase-prephenate dehydrogenase, of the above-described nucleic acid constructs, in particular the expression cassettes for generating genetically modified plants or for the transformation of plants, plant cells, plant tissues or plant parts. The preferred purpose of the use is to increase the fine chemical content of the plant or the plant parts, in particular the vitamin E, vitamin K or ubiquinone content, preferably the vitamin E content.

Depending on the choice of the promoter, expression may take place specifically in the leaves, in the seeds, in the petals or in other parts of the plant.

Accordingly, the invention further relates to a method for generating genetically modified organisms by introducing, into the genome of the starting organism, an above-described nucleic acid or an above-described nucleic acid construct.

The invention preferably relates to a method of transforming a plant, which comprises introducing expression cassettes comprising nucleic acid sequences encoding a chorismate mutase, prephenate dehydrogenase or a chorismate mutase-prephenate dehydrogenase into a plant cell or plant protoplasts and regenerating these to give intact plants.

The invention also relates to the genetically modified organisms, the genetic modification modifying the metabolite flux of the shikimate pathway over the wild type and the fine chemical content of the organism being modified over that of the wild type.

As mentioned above, the content of fine chemicals, in particular of vitamin E, vitamin K and ubiquinone, preferably of vitamin E, of preferred genetically modified organisms is increased over that of the wild type.

A genetically modified organism is to be understood as meaning, in accordance with the invention, in particular an organism in which the genetic modification, in the event that the starting organism contains the nucleic acid in question, increases the gene expression of a nucleic acid encoding a chorismate mutase, prephenate dehydrogenase or chorismate mutase-prephenate dehydrogenase over a wild type, or, in the event that the starting organism does not contain the nucleic acid in question, brings about the gene expression of a nucleic acid encoding a chorismate mutase, prephenate dehydrogenase or chorismate mutase-prephenate dehydrogenase over a wild type.

In a preferred embodiment, as mentioned above, photosynthetically active organisms such as, for example, cyanobacteria, mosses, algae or plants, especially preferably plants, are used as starting organisms and, accordingly, also as genetically modified organisms, as organisms and for generating organisms whose fine chemical content is increased over the wild type.

Such transgenic plants, their propagation material, and their plant cells, plant tissues or plant parts are a further subject matter of the present invention.

Plants for the purposes of the invention are, in particular, monocots and dicots.

Preferred plants are *Tagetes*, sunflower, *Arabidopsis*, tobacco, red pepper, soybeans, tomato, aubergine, bell pepper, carrot, potato, maize, saladings and cabbages, cereals, alfalfa, oats, barley, rye, wheat, triticale, sorghum and millet, rice, lucerne, flax, cotton, hemp, *Brassicaceae* such as, for example, oil seed rape or canola, sugarbeet, sugar cane, nut and grapevine species or wood species, such as, for example, aspen or yew.

Especially preferred are *Arabidopsis thaliana, Tagetes erecta, Brassica napus, Nicotiana tabacum*, canola, potatoes, and other oil crops such as, for example soybeans.

The genetically modified organisms, in particular plants, can be used as described above for the production of fine chemicals, in particular for the production of vitamin E, vitamin K and ubiquinone.

Genetically modified plants according to the invention which can be consumed by humans and animals and which have an increased content of fine chemicals, in particular an increased content of vitamin E, ubiquinone and/or vitamin K, preferably vitamin E, may also be used as foodstuffs or feedstuffs, for example directly or after processing in a manner known per se.

Increasing the fine chemicals content means for the purposes of the present invention the artificially acquired ability of increased biosynthesis of these compounds in the plant in comparison with the plant which has not been modified by genetic engineering over at least one plant generation.

An increased vitamin E content is to be understood as meaning, as a rule, an increased content of total tocopherol. However, an increased vitamin E content is also understood as meaning, in particular, a modified content of the above-described 8 compounds with tocopherol activity.

For example, the introduction of a chorismate mutase-prephenate dehydrogenase gene into plants surprisingly results in a particular increase in the tocotrienol content.

When the vitamin E content is increased, both the tocopherol content or the tocotrienol content may be increased. It is preferred to increase the tocopherol content. However, it is also possible under certain conditions preferentially to increase the tocotrienol content.

For example, the biosynthesis site of vitamin E, in plants, is, inter alia, the leaf tissue, so that leaf-specific expression of the nucleic acids according to the invention, in particular of the nucleic acids encoding a chorismate mutase, a prephenate dehydrogenase or a chorismate mutase-prephenate dehydrogenase, makes sense. However, this does not constitute a limitation since expression may also take place in a tissue-specific manner in all other parts of the plant, in particular in fatty seeds.

A further preferred embodiment thus relates to a seed-specific expression of the nucleic acids according to the invention, in particular the nucleic acids encoding a chorismate mutase, a prephenate dehydrogenase or a chorismate mutase-prephenate dehydrogenase.

In addition, constitutive expression of exogenous chorismate mutase, prephenate dehydrogenase or chorismate mutase-prephenate dehydrogenase genes is advantageous. On the other hand, inducible expression may also appear desirable.

Expression efficacy of the recombinantly expressed chorismate mutase, prephenate dehydrogenase or chorismate mutase-prephenate dehydrogenase gene can be determined for example in vitro by shoot meristem propagation. Also, changes in the nature and level of the expression of the chorismate mutase, prephenate dehydrogenase or chorismate mutase-prephenate dehydrogenase gene, and their effect on vitamin E biosynthesis, can be tested on test plants in greenhouse experiments.

The invention is now illustrated by the examples which follow, but not limited thereto:

General experimental conditions:

Sequence analysis of recombinant DNA

Recombinant DNA molecules were sequenced using a Licor laser fluorescence DNA sequencer (available from MWG Biotech, Ebersbach) using the method of Sanger (Sanger et al., Proc. Natl. Acad. Sci. USA 74 (1977), 5463-5467).

EXAMPLE 1

Cloning the tyrA Gene Encoding the *E. coli* K12 Chorismate Mutase-Prephenate Dehydrogenase The DNA encoding the tyrA gene was amplified from *E. coli* K12 by means of polymerase chain reaction (PCR) using a sense-specific primer (tyrA5' SEQ ID No. 10) and an antisense-specific primer (tyrA3' SEQ ID No. 9).

The PCR conditions were as follows:

The PCR was carried out in a 50 µl reaction mix comprising:

2 µl of an *E. coli* K12 cell suspension
0.2 mM DATP, dTTP, dGTP, dCTP
1.5 mM $Mg(OAc)_2$
5 µg of bovine serum albumin
40 pmol tyrA5'
40 pmol tyrA3'
15 µl 3.3× rTth DNA polymerase XL buffer (PE Applied Biosystems)
5 U rTth DNA polymerase XL (PE Applied Biosystems)

The PCR was carried out under the following cycle conditions:

Step 1: 5 minutes at 94° C. (denaturation)
Step 2: 3 seconds at 94° C.
Step 3: 1 minute at 55° C. (annealing)
Step 4: 2 minutes at 72° C. (elongation)
Steps 2 to 4 are repeated 30 times
Step 5: 10 minutes at 72° C. (post-elongation)
Step 6: 4° C. (waiting loop)

The amplicon was cloned into the PCR cloning vector pGEM-T (Promega) using standard methods. The identity of the amplicon generated was confirmed by sequencing using the M13F (−40) primer.

EXAMPLE 2

Generation of Expression Cassettes Comprising the tyrA Gene Encoding the *E. coli* K12 Chorismate Mutase-Prephenate Dehydrogenase Transgenic *Nicotiana tabacum* and *Arabidopsis thaliana* plants were generated which expressed the *E. coli* K12 chorismate mutase-prephenate dehydrogenase under the control of the constitutive CaMV (cauliflower mosaic virus) 35S promoter (Franck et al., Cell 21: 285-294, 1980). The basis of the plasmid generated for the constitutive expression of the *E. coli* K12 chorismate mutase-prephenate dehydrogenase was pBinAR-TkTp-10 (Ralf Badur, PhD Thesis, University of Göttingen, 1998). This vector is a derivative of pBinAR (Höfgen and Willmitzer, Plant Sci. 66: 221-230, 1990) and comprises the CaMV (cauliflower mosaic virus) 35S promoter (Franck et al., 1980), the termination signal of the octopine synthase gene (Gielen et al., EMBO J. 3: 835-846, 1984) and the DNA sequence encoding the transit peptide of the *Nicotiana tabacum* plastid transketolase. Cloning of the *E. coli* K12 chorismate mutase-prephenate dehydrogenase into this vector taking into consideration the correct reading frame generates a translational fusion of chorismate mutase-prephenate dehydrogenase with the plastid transit peptide. This causes the transgene to be transported into the plastids.

To construct this plasmid, the tyrA gene was isolated from plasmid pGEM-T/tyrA using the flanking SmaI or SalI restriction cleavage sites. This fragment was ligated into an SmaI/SalI-cut pBinAR-TkTp-10 using standard methods (see FIG. 2). This plasmid (pBinAR-TkTp-10/tyrA) was used to generate transgenic *Nicotiana tabacum* and *A. thaliana* plants.

Fragment A (529 bp) in FIG. 2 comprises the CaMV 35S promoter (nucleotides 6909 to 7437 of the cauliflower mosaic virus), Fragment B (245 bp) encodes the transit peptide of the *Nicotiana tabacum* transketolase, Fragment C (1232 Bp) encodes the *E. coli* K12 tyrA gene, and Fragment D (219 Bp) encodes the termination signal of the octopine synthase gene.

EXAMPLE 3

Generation of Nucleic Acid Constructs for Expressing the *E. coli* K12 Chorismate Mutase-Prephenate Dehydrogenase Under the Control of a Seed-Specific Promoter To generate chimeric DNA constructs for the generation of transgenic *Arabidopsis thaliana, Nicotiana tabacum* and *Brassica napus* plants which express the *E. coli* K12 chorismate mutase-prephenate dehydrogenase under the control of a seed-specific promoter, use was made of vector pPTVkanLeP-IPP-TP-9.

This vector is a derivative of pGPTVkan (D. Becker, E. Kemper, J. Schell, R. Masterson. *Plant Molecular Biology* 20: 1195-1197, 1992) whose uida gene had been deleted. Instead, the vector pPTVkanLeP-IPP-TP-9 contains the seed-specific promoter of the legumin B4 gene (Kafatos et al., Nuc. Acid. Res., 14(6):2707-2720, 1986), the sequence encoding the transit peptide of the *A. thaliana* plastid-specific isopentenyl pyrophosphate isomerase-2 (IPP-2) (Badur, unpublished) and the termination of the *A. tumefaciens* nopaline synthase (Depicker et al., J. Mol. Appl. Genet. 1, 561-73, 1982).

The nucleic acid fragment encoding the *E. coli* K12 tyrA was cloned into the vector pPTVkanLeP-IPP-TP-9 as SmaI/SalI fragment with blunt ends filled up with T4-polymerase (FIG. 3), giving rise to a translation fusion with the IPP-2 transit peptide. Thus, the import of chorismate mutase-prephenate dehydrogenase into the plastids was ensured. This plasmid (pPTVkanLeP-IPP-TP-9/TyrA) was used for generating transgenic *Nicotiana tabacum, A. thaliana* and *Brassica napus* plants.

Figure 3:
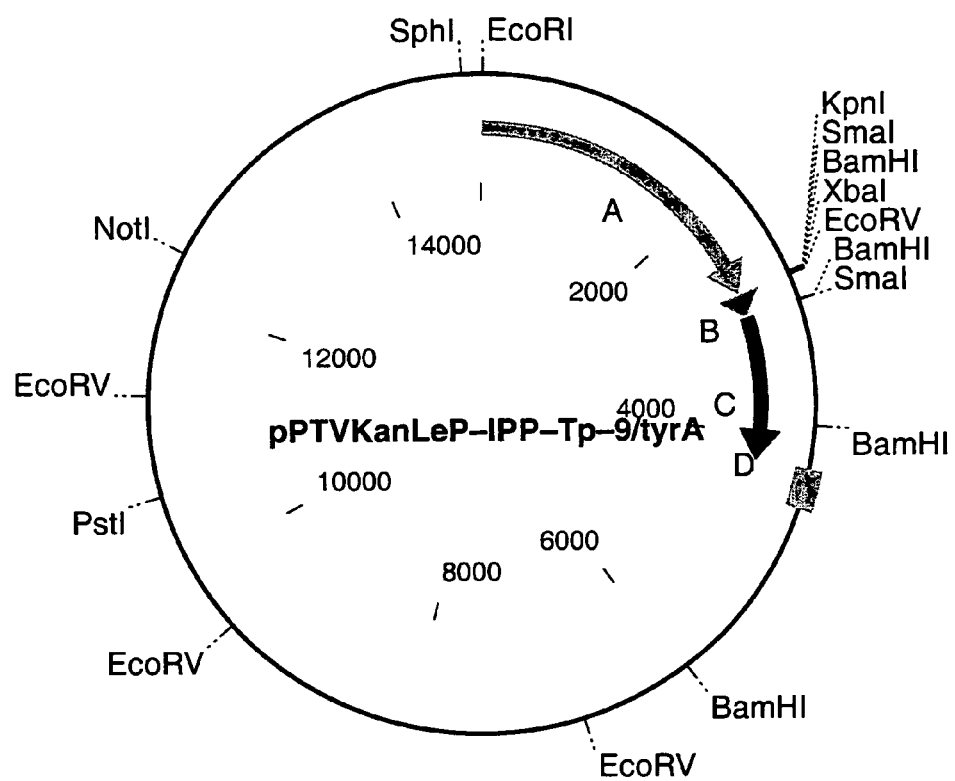

In FIG. 3, fragment A (2700 bp) comprises the promoter of the *Vicia faba* legumin B4 gene, fragment B (206 bp) encodes the transit peptide of the *A. thaliana* isopentenyl-pyrophosphate isomerase-2, fragment C (1234 bp) encodes the *E. coli* K12 tyrA gene, and fragment D (272 bp) encodes the termination signal of the nopaline synthase gene.

EXAMPLE 4

Generation of Transgenic *Arabidopis thaliana* Plants which Express the tyrA Gene Wild-type *Arabidopsis thaliana* plants (Columbia) were transformed with the *Agrobacterium tumefaciens* strain (GV3101 [pMP90]) on the basis of a modified vacuum infiltration method (Steve Clough and Andrew Bent. Floral dip: a simplified method for *Agrobacterium* mediated transformation of *A. thaliana*. Plant J 16(6):735-43, 1998; Bechtold, N. Ellis, J. and Pelltier, G., in: Planta *Agrobacterium*-mediated gene transfer by infiltration of adult *Arabidopsis thaliana* plants. CRAcad Sci Paris, 1993, 1144(2):204-212).

The *Agrobacterium tumefaciens* cells used had previously been transformed with the plasmids pBinAR-TkTp-10/tyrA and pPTVkanLeP-IPP-TP-9/tyrA (FIGS. 2 and 3).

Seeds of the primary transformants were selected on the basis of their resistance to antibiotics. Seedlings which were resistant to antibiotics were planted into soil, and the fully developed plants were used for biochemical analysis.

EXAMPLE 5

Generation of transgenic *Brassica napus* Plants which Express the tyrA Gene The generation of transgenic oil seed rape plants followed in principle a procedure of Bade, J. B. and Damm, B. (in Gene Transfer to Plants, Potrykus, I. and Spangenberg, G., eds, Springer Lab Manual, Springer Verlag, 1995, 30-38), which also indicates the composition of the media and buffers used.

The transformations were carried out with the *Agrobacterium tumefaciens* strain GV3101 [pMP90]. The plasmid pPTVkanLeP-IPP-TP-9/tyrA was used for the transformation (FIG. 3). Seeds of *Brassica napus* var. Westar were surface-sterilized with 70% ethanol (v/v), washed for 10 minutes at 55° C. in water, incubated for 20 minutes in 1% strength hypochlorite solution (25% v/v Teepol, 0.1% v/v Tween 20) and washed six times with sterile water for in each case 20 minutes. The seeds were dried for three days on filter paper, and 10-15 seeds were germinated in a glass flask containing 15 ml of germination medium. Roots and apices were removed from several seedlings (approx. size 10 cm), and the hypocotyls which remained were cut into sections approx. 6 mm in length. The approx. 600 explants thus obtained were washed for 30 minutes in 50 ml of basal medium and transferred into a 300 ml flask. After addition of 100 ml callus induction medium, the cultures were incubated for 24 hours at 100 rpm.

An overnight culture of the agrobacterium strain was set up in Luria broth medium supplemented with kanamycin (20 mg/l) at 29° C., and 2 ml of this were incubated in 50 ml of Luria broth medium without kanamycin for 4 hours at 29° C. until an $OD_{600}$ of 0.4-0.5 was reached. After the culture had been pelleted for 25 minutes at 2000 rpm, the cell pellet was resuspended in 25 ml of basal medium. The bacterial concentration of the solution was brought to an $OD_{600}$ of 0.3 by adding more basal medium.

The callus induction medium was removed from the oil seed rape explants using sterile pipettes, 50 ml of agrobacterial solution were added, and the reaction was mixed carefully and incubated for 20 minutes. The agrobacterial suspension was removed, the oil seed rape explants were washed for 1 minute with 50 ml of callus induction medium, and 100 ml of callus induction medium were subsequently added. Coculturing was carried out for 24 hours on an orbital shaker at 100 rpm. Coculturing was stopped by removing the callus induction medium, and the explants were washed twice for in each case 1 minute with 25 ml and twice for 60 minutes with in each case 100 ml of wash medium at 100 rpm. The wash medium together with the explants was transferred into 15 cm Petri dishes, and the medium was removed using sterile pipettes.

For regeneration, in each case 20 to 30 explants were transfered into 90 mm Petri dishes containing 25 ml of shoot induction medium supplemented with kanamycin. The Petri dishes were sealed with 2 layers of Leukopor and incubated at 25° C. and 2000 lux at photoperiods of 16 hours light/8 hours darkness. Every 12 days, the calli which developed were transfered to fresh Petri dishes containing shoot induction medium. All further steps for the regeneration of intact plants were carried out as described by Bade, J. B and Damm, B. (in: Gene Transfer to Plants, Potrykus, I. and Spangenberg, G., eds, Springer Lab Manual, Springer Verlag, 1995, 30-38).

EXAMPLE 6

Generation of Transgenic *Nicotiana tabacum* Plants which Express the tyrA Gene Ten ml of YEB medium supplemented with antibiotic (5 g/l beef extract, 1 g/l yeast extract, 5 g/l peptone, 5 g/l sucrose and 2 MM $MgSO_4$) were inoculated with a colony of *Agrobacterium tumefaciens* and the culture was grown overnight at 28° C. The cells were pelleted for 20 minutes at 4° C., 3500 rpm, using a bench-top centrifuge and then resuspended under sterile conditions in fresh YEB medium without antibiotics. The cell suspension was used for the transformation.

The sterile-grown wild-type plants were obtained by vegetative propagation. To this end, only the tip of the plant was cut off and transfered to fresh 2MS medium in a sterile preserving jar. As regards the rest of the plant, the hairs on the upper side of the leaves and the central veins of the leaves were removed. Using a razor blade, the leaves were cut into sections of approximate size 1 $cm^2$. The agrobacterial culture was transferred into a small Petri dish (diameter 2 cm). The leaf sections were briefly drawn through this solution and placed with the underside of the leafs on 2MS medium in Petri dishes (diameter 9 cm) in such a way that they touch the medium. After two days in the dark at 25° C., the explants were transfered to plates with callus induction medium and warmed at 28° C. in a controlled-environment cabinet. The medium had to be changed every 7-10 days. As soon as calli formed, the explants were transferred into sterile preserving jars onto shoot induction medium supplemented with claforan (0.6% BiTec agar (w/v), 2.0 mg/l zeatin ribose, 0.02 mg/l naphthylacetic acid, 0.02 mg/l gibberellic, 0.25 g/ml claforan, 1.6% glucose (w/v) and 50 mg/l kanamycin). Organogenesis started after approximately one month and it was possible to cut off the shoots which had formed. The shoots were grown on 2MS medium supplemented with claforan and selection marker. As soon as a substantial root ball had developed, it was possible to pot up the plants in seed compost.

EXAMPLE 7

Characterization of the Transgenic Plants of Examples 4, 5 and 6

The tocopherol and tocotrienol contents in leaves and seeds of the plants transformed with the above-described constructs (*Arabidopsis thaliana, Brassica napus* and *Nicotiana tabacum*) were analyzed. To this end, the transgenic plants were grown in the greenhouse, and plants which expressed the gene encoding the *E. coli* K12 chorismate mutase-prephenate dehydrogenase are analyzed at Northern and Western level. The tocopherol content and the tocotrienol content of these plants in the leaves and seeds were determined by HPLC. In all cases, the tocopherol and/or tocotrienol content in transgenic plants which additionally express a tyrA gene was increased in comparison with untransformed plants.

Table 1A (young leaves) and 1B (senescent leaves) show the contents [μg/g FW] of α-tocopherol, γ-tocopherol, α-tocotrienol and total vitamin E in leaves of different ages in *Nicotiana tabacum*, cv. SNN wild type (data shown: MW±SD, n=9) and plants which overexpress the *E. coli* Tyr A gene.

TABLE A

Young leaves

| | α-Tocopherol | | γ-Tocopherol | | α-Tocotrienol | Total vitamin E | |
|---|---|---|---|---|---|---|---|
| Wild-type SNN | 19.0 | ±2.9 | 0.31 | ±0.03 | <0.20 | 19.3 | ±2.8 |
| Line 8 | 27.6 | | 1.25 | | 1.03 | 30.0 | |
| Line 15 | 35.7 | | 0.73 | | 1.00 | 37.4 | |
| Line 54 | 32.3 | | 4.60 | | 1.60 | 38.7 | |
| Line 86 | 15.7 | | 4.47 | | 0.98 | 21.4 | |
| Line 113 | 32.3 | | 0.71 | | 0.62 | 33.6 | |

TABLE B

Senescent leaves

| | α-Tocopherol | | γ-Tocopherol | | α-Tocotrienol | Total vitamin E | |
|---|---|---|---|---|---|---|---|
| Wild-type SNN | 32.9 | ±2.1 | 0.31 | ±0.05 | <0.20 | 33.1 | ±2.1 |
| Line 8 | 50.7 | | 0.69 | | 2.69 | 54.2 | |
| Line 15 | 54.7 | | 0.69 | | 0.81 | 56.2 | |
| Line 54 | 37.0 | | 2.60 | | 0.35 | 40.0 | |
| Line 86 | 36.5 | | 1.51 | | 0.43 | 38.4 | |
| Line 113 | 46.2 | | 0.45 | | 2.29 | 48.9 | |

EXAMPLE 8

Cloning a Subfragment of the Gene Encoding the *Arabidopsis thaliana* Chorismate Mutase-1 which is Expressed in the Plastids The DNA sequence coding the transit peptide of the chorismate mutase-1 gene was amplified by polymerase chain reaction (PCR) from *Arabidopsis thaliana* using a sense-specific primer (CM-1TP 5' SEQ ID No. 11) and an antisense-specific primer (CM-1TP 3' SEQ ID No. 12).

The PCR conditions were as follows:
The PCR was carried out in a 50 µl reaction mix comprising:
  2 µl of an *Arabidopsis thaliana* cDNA
  0.2 mM DATP, dTTP, dGTP, dCTP
  1.5 mM Mg(OAc)$_2$
  5 µg of bovine serum albumin
  40 pmol CM-1TP 5' primer
  40 pmol CM-1TP 3' primer
  15 µl 3.3µ rTth DNA polymerase XL buffer (PE Applied Biosystems)
  5 U rTth DNA polymerase XL (PE Applied Biosystems)
The PCR was carried out under the following cycle conditions:
  Step 1: 5 minutes at 94° C. (denaturation)
  Step 2: 3 seconds at 94° C.
  Step 3: 1 minute at 55° C. (annealing)
  Step 4: 2 minutes at 72° C. (elongation)
  Steps 2 to 4 are repeated 30 times
  Step 5: 10 minutes at 72° C. (post-elongation)
  Step 6: 4° C. (waiting loop)
The amplicon was cloned into the PCR cloning vector pCR-script (stratagene) using standard methods. The identity of the amplicon generated was confirmed by sequencing using a vector-specific primter.

EXAMPLE 9

Cloning the Gene Encoding the *Arabidopsis thaliana* Chorismate Mutase-2 which is Expressed in the Cytosol The DNA encoding the chorismate mutase-2 gene was amplified from *Arabidopsis thaliana* by means of polymerase chain reaction (PCR) using a sense-specific primer (CM-2 5' SEQ ID No. 13) and an antisense-specific primer (CM-2 3' SEQ ID No. 14).

The PCR conditions were as follows:
The PCR was carried out in a 50 µl reaction mix comprising:
  2 µl of an *Arabidopsis thaliana* cDNA
  0.2 mM DATP, dTTP, dGTP, dCTP
  1.5 mM Mg(OAc)$_2$
  5 µg of bovine serum albumin
  40 pmol CM-2 5' primer
  40 pmol CM-2 3' primer
  15 µl 3.3µ rTth DNA polymerase XL buffer (PE Applied Biosystems)
  5 U rTth DNA polymerase XL (PE Applied Biosystems)
The PCR was carried out under the following cycle conditions:
  Step 1: 5 minutes at 94° C. (denaturation)
  Step 2: 3 seconds at 94° C.
  Step 3: 1 minute at 55° C. (annealing)
  Step 4: 2 minutes at 72° C. (elongation)
  Steps 2 to 4 are repeated 30 times
  Step 5: 10 minutes at 72° C. (post-elongation)
  Step 6: 4° C. (waiting loop)
The amplicon was cloned into the PCR cloning vector pGEM-T (Promega) using standard methods. The identity of the amplicon generated was confirmed by sequencing using the M13F (−40) primer.

EXAMPLE 10

Generation of the Chimeric Gene Construct CM-1-TP-CM-2 Composed of the DNA Sequence Encoding the Transit Peptide (TP) of Chorismate Mutase-1 (CM-1) and the DNA Sequence Encoding Chorismate Mutase-2 (CM-2)

To generate the chimeric gene CM-1-TP-CM-2, the plasmid pCR-Script/CM-1-TP was digested with the restriction enzyme NcoI/SalI.

The DNA fragment of CM-2 which had been isolated from plasmid pGEM-Teasy/CM-2 by means of the restriction enzymes NcoI/SalI was ligated into this plasmid. The translation of this chimeric DNA construct (SEQ ID No. 5) (pCR-Script/AtCM-1TP-AtCM-2, FIG. 4) results in the formation of a fusion protein in which the transit peptide of CM-1 is combined with CM-2 (SEQ ID No. 6).

EXAMPLE 11

Production of Plant Expression Cassettes Comprising the Chimeric Gene CM-1-TP-CM-2

Transgenic plants were generated which express the chimeric gene CM-1-TP-CM2 from *A. thaliana* firstly under the control of the constitutive CaMV (cauliflower mosaic virus) 35S promoter (Franck et al., Cell 21: 285-294, 1980) and secondly under the control of the seed-specific promoter of the Vicia faba legumin gene (Kafatos et al., Nuc. Acid. Res., 14(6): 2707-2720, 1986).

Figure 4:
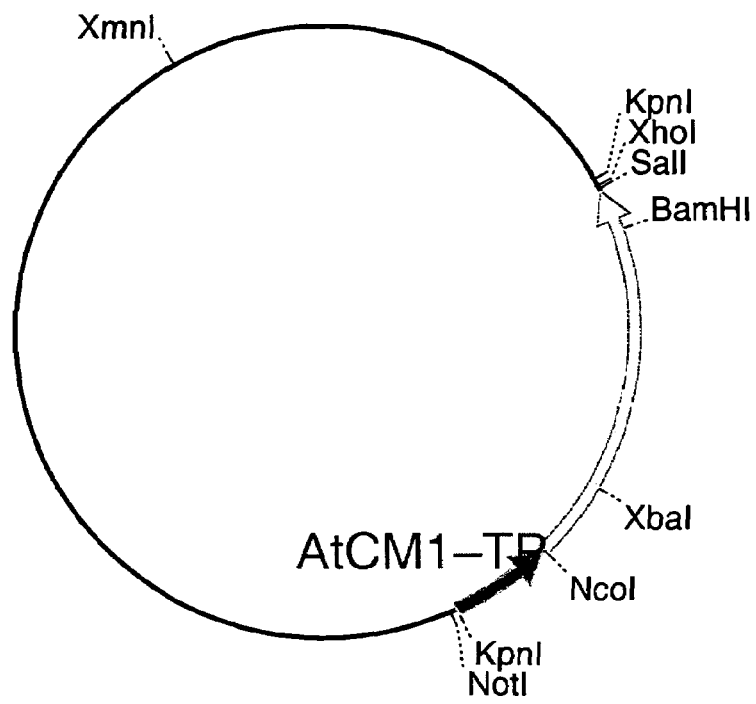
Figure 5:
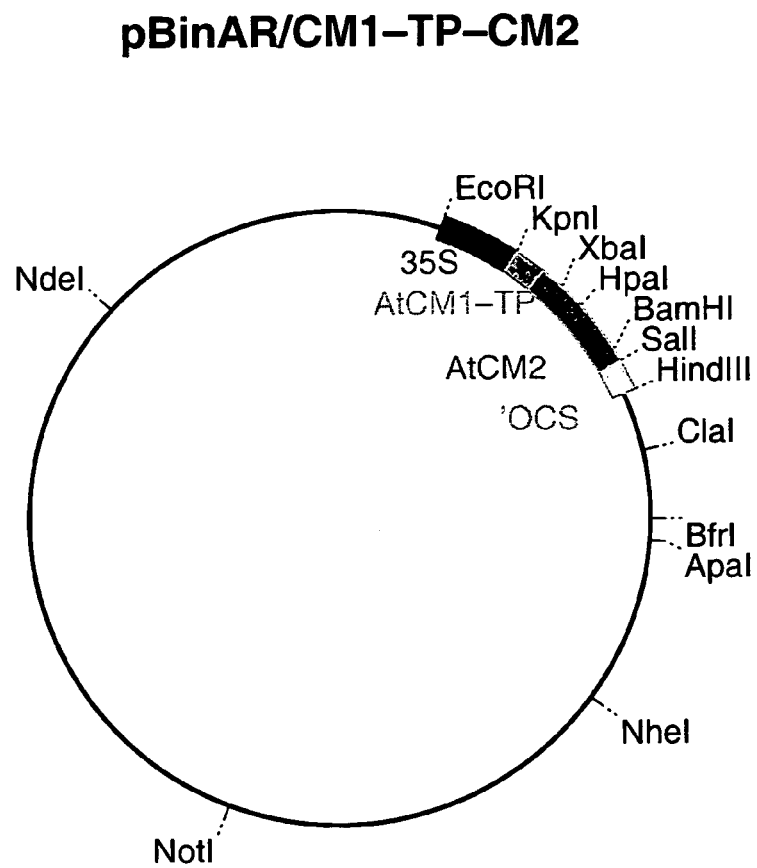

The basis of the plasmid generated for the constitutive expression of the chimeric gene CM-1TP-CM-2 was the vector pBinAR (Höfgen and Willmitzer, Plant Sci. 66: 221-230, 1990). This vector contains the CaMV (cauliflower mosaic virus) 35S promoter (Franck et al., 1980) and the termination signal of the octopine synthase gene (Gielen et al., EMBO J. 3: 835-846, 1984). To generate this plasmid, the chimeric gene CM-1-TP-CM2 was isolated from plasmid pCR-script/AtCM-1TP-AtCM-2 using the flanking restriction cleavage sites KpnI/SalI (FIG. 4). Using standard methods, this fragment was ligated into a KpnI/SalI-cut pBinAR. The resulting plasmid (pBinAR/CM-1TP/CM-2, FIG. 5) was used for generating transgenic Arabidopsis thaliana and Nicotiana tabacum.

Figure 6:
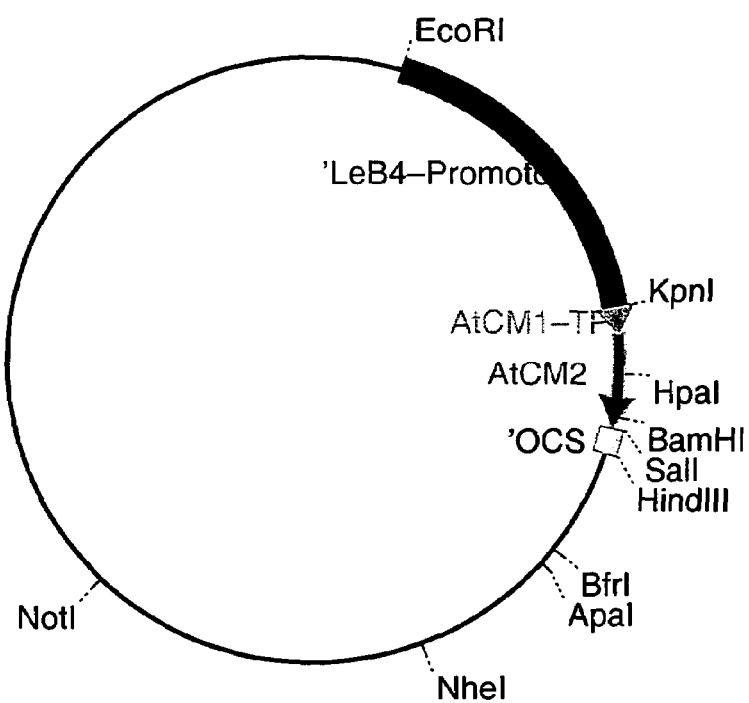

To produce a plasmid which allows the seed-specific expression of the chimeric gene CM-1TP/CM-2 in plants, the seed-specific promoter of the legumin B4 gene (Kafatos et al., Nuc. Acid. Res., 14(6):2707-2720, 1986) was used. The 2.7 kb fragment of the legumin B4 gene promoter was isolated from plasmid pGEMTeasy/1ePNOS using the EcoRI cleavage site which flanks the promoter 5' and the KpnI cleavage site which flanks the promoter 3'. Plasmid pBinAR/CM-1TP/CM-2 was also treated with the restriction enzymes EcoR1 and Kpn1. As a consequence, the CaMV 35S promoter was excised from this plasmid (see FIG. 5). The legumin gene promoter was subsequently cloned into this vector as EcoR1/Kpn1 fragment, giving rise to a plasmid which placed expression of the chimeric gene CM-1TP-CM-2 under the control of this seed-specific promoter (see FIG. 6). This plasmid (pBinLeP/CM-1TP/CM-2) was used for generating transgenic Arabidopsis thaliana and Nicotiana tabacum plants.

EXAMPLE 12

Generation of Transgenic Arabidopis thaliana Plants which Express the Chimeric Gene CM-1-TP-CM-2

The plants were generated analogously to Example 4 using the plasmids (pBinAR/AtCM-1TP/CM-2) and (pBinLeP/CM-1TP/CM-2).

EXAMPLE 13

Generation of Transgenic Brassica napus Plants which Express the tyrA Gene

The plants were generated analogously to Example 5 using the plasmids (pBinAR/AtCM-1TP/CM-2) and (pBinLeP/CM-1TP/CM-2).

EXAMPLE 14

Generation of Transgenic Nicotiana tabacum Plants which Express the tyrA Gene

The plants were generated analogous to Example 6 using the plasmids (pBinAR/AtCM-1TP/CM-2) and (pBinAR1eP/CM-1TP/CM-2).

EXAMPLE 15

Characterizing the Transgenic Plants of Examples 12, 13 and 14

The tocopherol and tocotrienol contents in leaves and seeds of the plants transformed with the above-described constructs (Arabidopsis thaliana, Brassica napus and Nicotiana tabacum) were analyzed. To this end, the transgenic plants were grown in the greenhouse, and plants which expressed the gene encoding the cytosolic chorismate mutase are analyzed at Northern and Western level. The tocopherol content and the tocotrienol content of these plants in the leaves and seeds were determined by HPLC. In all cases, the tocopherol and/or tocotrienol content in transgenic plants which additionally express chorismate mutase genes was increased in comparison with untransformed plants.

We claim:

1. A method for the preparation of vitamin E comprising introducing into a plant a polynucleotide sequence encoding a chorismate mutase-prephenate dehydrogenase, expressing the polynucleotide, and isolating vitamin B from the plant, wherein the polynucleotide sequence comprises a nucleic acid sequence which encodes a protein comprising the amino acid sequence of SEQ ID NO. 2 or an amino acid sequence having at least 90% sequence identity with the sequence of SEQ ID NO. 2 wherein the protein has the enzymatic activity of a chorismate mutase-prephenate dehydrogenase.

2. The method as claimed in claim 1, wherein the nucleic acid sequence is of bacterial origin.

3. The method as claimed in claim 1, wherein the nucleic acid sequence comprises the sequence shown in SEQ ID NO. 1.

* * * * *

UNITED STATES PATENT AND TRADEMARK OFFICE
CERTIFICATE OF CORRECTION

| | | |
|---|---|---|
| PATENT NO. | : 7,332,649 B2 | Page 1 of 1 |
| APPLICATION NO. | : 10/297661 | |
| DATED | : February 19, 2008 | |
| INVENTOR(S) | : Ralf Badur et al. | |

It is certified that error appears in the above-identified patent and that said Letters Patent is hereby corrected as shown below:

In column 45, one line 15, "the polynucleotide, and isolating vitamin B from the plant," should read -- the polynucleotide, and isolating vitamin E from the plant, --.

Signed and Sealed this

Twenty-sixth Day of August, 2008

JON W. DUDAS
*Director of the United States Patent and Trademark Office*